United States Patent
Crozet et al.

(10) Patent No.: US 6,554,834 B1
(45) Date of Patent: Apr. 29, 2003

(54) SLOTTED HEAD PEDICLE SCREW ASSEMBLY

(75) Inventors: Yves Crozet, Ramsey, NJ (US); Gregory Martin, New York, NY (US)

(73) Assignee: Stryker Spine (FR)

( * ) Notice: Subject to any disclaimer, the term of this patent is extended or adjusted under 35 U.S.C. 154(b) by 0 days.

(21) Appl. No.: 09/414,272

(22) Filed: Oct. 7, 1999

(51) Int. Cl.[7] .............................................. A61B 17/56
(52) U.S. Cl. ............................. 606/65; 606/61; 606/72; 606/73
(58) Field of Search .......................... 606/61, 60, 69, 606/65, 70, 71, 72, 73, 54, 59, 66, 104; 623/16.11, 17.11

(56) References Cited

U.S. PATENT DOCUMENTS

| | | | |
|---|---|---|---|
| 4,484,570 A | * 11/1984 | Sutter et al. | 606/61 |
| 4,805,602 A | 2/1989 | Puno et al. | 128/69 |
| 4,946,458 A | 8/1990 | Harms et al. | 606/61 |
| 5,129,388 A | 7/1992 | Vignaud et al. | 606/61 |
| 5,176,678 A | 1/1993 | Tsou | 606/61 |
| 5,190,543 A | 3/1993 | Schlapfer | 606/61 |
| 5,207,678 A | 5/1993 | Harms et al. | 606/61 |
| 5,217,497 A | 6/1993 | Mehdian | 623/17 |
| 5,344,422 A | 9/1994 | Frigg | 606/61 |
| 5,360,431 A | 11/1994 | Puno et al. | 606/72 |
| 5,439,381 A | * 8/1995 | Cohen | 433/173 |
| 5,443,467 A | 8/1995 | Biedermann et al. | 606/65 |
| 5,466,237 A | 11/1995 | Byrd, III et al. | 606/61 |
| 5,474,555 A | 12/1995 | Puno et al. | 606/73 |
| 5,476,464 A | 12/1995 | Met-Stavenhagen et al. | 606/61 |
| 5,496,321 A | 3/1996 | Puno et al. | 600/61 |
| 5,531,746 A | 7/1996 | Errico et al. | 606/61 |
| 5,549,608 A | 8/1996 | Errico et al. | 606/61 |
| 5,554,157 A | 9/1996 | Errico et al. | 6065/61 |
| 5,586,984 A | 12/1996 | Errico et al. | 606/61 |
| 5,647,873 A | 7/1997 | Errico et al. | 606/61 |
| 5,669,911 A | 9/1997 | Errico et al. | 606/61 |
| 5,672,176 A | 9/1997 | Biedermann et al. | 606/61 |
| 5,690,630 A | 11/1997 | Errico et al. | 606/61 |
| 5,725,527 A | 3/1998 | Bierdermann et al. | 606/61 |
| 5,733,285 A | 3/1998 | Errico et al. | 606/61 |
| 5,733,286 A | * 3/1998 | Errico et al. | 606/61 |
| 5,797,911 A | 8/1998 | Sherman et al. | 606/61 |
| 5,873,878 A | * 2/1999 | Harms et al. | 606/61 |
| 5,879,350 A | * 3/1999 | Sherman et al. | 606/61 |
| 5,882,350 A | 3/1999 | Ralph et al. | 606/61 |
| 5,885,286 A | 3/1999 | Sherman et al. | 606/61 |
| 5,891,145 A | 4/1999 | Morrison et al. | 606/61 |
| 6,063,090 A | * 5/2000 | Schlapfer | 606/61 |
| 6,074,391 A | * 6/2000 | Metz-Stavenhagen et al. | 606/61 |
| 6,077,262 A | * 6/2000 | Schlapfer et al. | 606/61 |

FOREIGN PATENT DOCUMENTS

WO    WO 88/03781    6/1988

* cited by examiner

*Primary Examiner*—Pedro Philogene
(74) *Attorney, Agent, or Firm*—Lerner, David, Littenberg, Krumholz & Mentlik, LLP

(57) ABSTRACT

A pedicle screw assembly includes a fastener having an expandable head. The expandable head has an outer surface including a convex portion, a recess having an inner surface and defining an inner dimension, and at least one slot extending between the inner and outer surfaces thereof. The assembly also has an insert positionable at least partially in the recess having an outer surface defining an outer dimension that is greater than the inner dimension of the recess. The assembly includes a coupling element including a rod receiving opening, a bore for the fastener, and a seat for receiving the head of the fastener and allowing the fastener and coupling element to pivot relative to one another before being locked in place. After an orthopedic rod is positioned within the coupling element, a locking element associated with the coupling element locks the orthopedic rod in the rod-receiving opening. The locking element applies a force onto the rod to in turn force the insert into the recess of the expandable head for expanding the outer surface of the head against the seat of the coupling element and locking the coupling element and fastener from further pivotal movement relative to one another.

78 Claims, 23 Drawing Sheets

SLOTTED HEAD PEDICLE SCREW ASSEMBLY

FIELD OF THE INVENTION

The present invention relates to spinal fixation devices and more specifically relates to a pedicle screw assembly having a pedicle screw with an expandable head In a preferred embodiment, the assembly includes a coupling element having a seat for receiving the head of the screw and allowing polyaxial movement of the screw relative to the coupling element, and an insert for expanding the head of the pedicle screw against the seat of the coupling element so as to prevent movement of the coupling element and pedicle screw relative to one another.

BACKGROUND OF THE INVENTION

The spinal column is a highly complex system of bones and connective tissues that provides support for the body and protects the delicate spinal column and nerves. The spinal column includes a series of vertebrae stacked one atop the other, whereby each vertebral body includes a relatively strong bone portion forming the outside surface of the body (cortical) and a relatively weak bone portion forming the center of the body (cancellous). Situated between each vertebral body is an intervertebral disc that provides for cushioning and dampening of compressive forces applied to the spinal column. The vertebral canal containing the delicate spinal cords and nerves is located just posterior to the vertebral bodies.

Various types of spinal column disorders are known and include scoliosis (abnormal lateral curvature of the spine), kyphosis (abnormal forward curvature of the spine, usually in the thoracic spine), excess lordosis (abnormal backward curvature of the spine, usually in the lumbar spine), spondylolisthesis (forward displacement of one vertebra over another, usually in a lumbar or cervical spine) and other disorders caused by abnormalities, disease or trauma, such as ruptured or slipped discs, degenerative disc disease, fractured vertebra, and the like. Patients that suffer from such conditions usually experience extreme and debilitating pain as well as diminished nerve function.

The present invention involves a technique commonly referred to as spinal fixation whereby surgical implants are used for fusing together and/or mechanically immobilizing adjacent vertebrae of the spine. Spinal fixation may also be used to alter the alignment of the adjacent vertebrae relative to one another so as to alter the overall alignment of the spine. Such techniques have been used effectively to treat the above-described conditions and, in most cases, to relieve pain suffered by the patient. However, as will be set forth in more detail below, there are some disadvantages associated with current fixation devices.

One particular spinal fixation technique includes immobilizing the spine by using orthopedic rods, commonly referred to as spine rods, that run generally parallel to the spine. This is accomplished by exposing the spine posteriorly and fastening bone screws to the pedicles of the appropriate vertebrae. The pedicle screws are generally placed two per vertebra, one at each pedicle on either side of the spinous process, and serve as anchor points for the spine rods. Clamping elements adapted for receiving a spine rod therethrough are then used to join the spine rods to the screws. The aligning influence of the rods forces the spine to conform to a more desirable shape. In certain instances, the spine rods may be bent to achieve the desired curvature of the spinal column.

U.S. Pat. No. 5,129,388 to Vignaud et al. discloses a spinal fixation device including a pedicle screw having a U-shaped head rigidly connected to the screw. The U-shaped head includes a U-shaped channel for receiving a spine rod therein. The U-shaped head is internally threaded so that a set screw having external threads may be screwed therein. After the pedicle screw has been inserted into bone and the spine rod is positioned in the U-shaped channel, the set screw is threaded into the internal threads of the coupling element for securing the spine rod in the U-shaped channel and blocking relative movement between the spine rod and the pedicle screw. The fixation device also includes a cap covering an upper portion of the U-shaped element to prevent the arms of the U-shaped element from spreading upon threading the set screw into the U-shaped head.

Surgeons have frequently encountered considerable difficulty when attempting to insert spinal fixation devices such as those disclosed in the above-mentioned '388 patent. For example, surgeons have frequently been unable to efficiently and adequately place the spine rod into the U-shaped heads of the bone screws. This is because the U-shaped heads of the screws are often not aligned with one another due to curvature in spines and the different orientations of the pedicles being instrumented. The spine rods are often bent in multiple planes in order to couple the pedicle screws to the rod, which may lead to weaker connections with the rod. These problems also result in significantly longer operations, thereby increasing the likelihood of complications associated with surgery.

In response to the problems noted in the '388 patent, U.S. Pat. No. 5,733,286 to Errico et al., U.S. Pat. No. 5,672,176 to Biedermann et al., and U.S. Pat. No. 5,476,464 to Metz-Stavenhagen disclose polyaxial spinal fixation devices wherein the anchoring element fixed to the bone has a spherically-shaped head. The fixation devices in the subject patents also have orthopedic rod capturing assemblies for securing orthopedic rods in the capturing assemblies and connecting the rods with the anchoring elements. The spherically shaped heads of the anchoring elements permit movement of the anchoring elements relative to the orthopedic rod capturing assemblies. However, the above-mentioned patents do not solve all of the deficiencies noted in the Vignaud '388 patent because the respective spinal fixation devices may shift following insertion. This is due primarily to the fact that there is insufficient surface area contact between the spherically-shaped heads of the anchoring elements and the rod capturing assemblies. In addition, the devices are complex and are difficult to manufacture.

Other polyaxial bone fixation devices are taught in International Patent Publication WO 88/03781. This publication describes a device for securing bone screws in openings in an osteosynthesis plate. The head of the bone screw is provided with longitudinal grooves that enable the head to expand after being positioned in one of the openings in the plate. After a screw has been inserted through one of the openings, an adjusting screw is threaded into a bore at the top of the head for expanding the head. The outer surface of the expanded head presses against the opening in the plate so as to secure the screw to the plate. U.S. Pat. No 4,484,570 also discloses a bone screw used in conjunction with a plate wherein the screw has a head with a central opening and slots that subdivide the head into tongues. An expander having a conical surface is inserted into the central opening of the head for expanding the head and locking the screw in relation to the plate. However, the WO 88/03781 and U.S. Pat. No. 4,484,570 references concern bone plates and not spinal fixation devices using orthopedic rods.

In spite of the above-mentioned devices, there remains room for improvement of prior art spinal fixation devices in the manner of locking the screw head, the complexity of use, difficulty in properly positioning the orthopedic rod and the rod-capturing assemblies, the required manipulation of the many parts associated with some complex devices and post-operative movement of the rod-capturing assemblies relative to the bone anchoring elements due to the weak interfaces between the two.

SUMMARY OF THE INVENTION

In accordance with certain preferred embodiments of the present invention, a pedicle screw assembly includes a fastener having a tip end for insertion into bone and an expandable head at the opposite end thereof. The head may be expandable by virtue of the material of which it is made or its design. One preferred design for an expandable head includes a head having one or more slots formed therein. In this embodiment, the expandable head preferably has an outer surface including a convex portion, a recess defining an inner surface having an inner dimension, and at least one slot extending between the inner and outer surfaces thereof for allowing expansion of the head. The assembly also includes an insert that can be positioned at least partially in the recess of the head. The insert desirably has an outer surface including an outer dimension that is greater than the inner dimension of the recess. In certain embodiments, the insert may be rotatable with the recess of the head.

The pedicle screw assembly also has a coupling element for coupling the pedicle screw to an orthopedic rod. The coupling element preferably includes a bore extending therethrough for receiving the fastener, and a seat for receiving the head of the fastener. The seat may include a concave portion for receiving the convex portion of the head and for allowing the fastener and the coupling element to pivot relative to one another before being locked to prevent further pivotal movement. The assembly may also include a locking element associated with the coupling element for locking the orthopedic rod in the coupling element after the rod has been positioned therein. The locking element is desirably adapted for forcing the insert into the recess of the head so that the outer dimension of the insert bears against the inner dimension of the head, whereby the head expands against the seat of the coupling element for preventing further pivotal movement of the coupling element relative to the fastener.

The expandable head of the fastener provides for an improved level of surface contact between the head and the seat of the coupling element. This increased level of surface contact results in a more secure locking force being generated. In addition, the locking force is increased by the friction force, which acts at the interface between the head of the fastener and the coupling element. This friction force is proportional to the normal force of the head of the fastener on the seat of the coupling element and thus increases as the insert acts to expand the head of the fastener. As a result, the likelihood of post-operative shifting and/or movement of a spine rod or coupling element relative to one or more of the bone fasteners is significantly reduced. Thus, the present invention provides for a more reliable spinal fixation device and overcomes the post-operative shifting problems seen in prior art devices. Moreover, the pedicle screw assembly of the present invention has fewer parts. As a result, implantation operations are greatly simplified and the possibility of a component being dropped inside a patient's body greatly reduced.

In certain preferred embodiments, the fastener is a pedicle bone screw having external threads extending from a tip end of the screw toward the head. The fastener may have one or more holes in the threaded portion therein for receiving bone graft material as disclosed in U.S. Pat. No. 4,484,570 to Sutter. Instead of using a screw for securing the screw to bone, in other preferred embodiments the fastener may includes a hook-shaped anchoring element as disclosed in above-mentioned U.S. Pat. No. 5,476,464 to Metz-Stavenhagen. The fastener may also be a structure having barbs on an outer surface thereof, whereby the fastener is forced into bone and the barbs prevent the fastener from being withdrawn from the bone. The fastener preferably includes a neck between the head and the tip end, the neck desirably being located adjacent the head. The neck includes a concave surface and has a diameter that is generally smaller than the diameter of the threaded portion of the fastener. The head of the fastener preferably includes a recess defining an inner surface having an inner dimension. The head also includes a plurality of slots extending between the inner and outer surfaces of the head. The fastener preferably has a longitudinal axis extending from the tip end to the head with the recess and the inner and outer surfaces thereof being centered on the longitudinal axis. The slots generally commence at the top surface of the head and extend toward the tip end of the fastener in directions substantially parallel to the longitudinal axis. The plurality of slots generally subdivide the head into two or more flexible arms at the upper end of the fastener. In one preferred embodiment, the head has six slots formed therein for subdividing the head into six flexible arms. The flexible arms are desirably adapted for flexing away from the longitudinal axis for expanding the outer surface of the head. The flexible arms are also capable of flexing toward the longitudinal axis for compressing the head, so as to reduce the outer dimension of the head and allow for assembly of the fastener into the coupling element.

The expandable head also preferably includes at least one tab extending into the recess for at least partially securing the insert in the recess. The tabs are preferably formed at upper ends of the flexible arms, whereby each flexible arm desirably includes one tab. The flexible arms are generally arranged in a substantially annular configuration around the circumference of the recess with the tabs extending into the recess for securing the insert.

The insert preferably has an upper end and a lower end and a longitudinal axis extending between the upper and lower ends. The insert also preferably has an outer surface and a flange extending around the outer surface, between the upper and lower ends thereof. In preferred embodiments, the flange lies in a plane substantially perpendicular to the longitudinal axis of the insert. The flange preferably defines the outer dimension of the insert, i.e., the section of the insert having the largest diameter. In other words, the flange provides the largest diameter portion of the insert. When viewed from the side or in a cross-sectional side view, the outer surface of the insert tapers inwardly from the flange toward the lower end thereof. In certain embodiments, the lower end of the insert is substantially spherical in shape. However, in other preferred embodiments, the lower end of the insert is substantially flat. The upper end of the insert preferably has a radial surface that is adapted for engaging the orthopedic rod. The radial surface of the upper end insures good surface contact between the rod and the insert, regardless of the angle of the insert relative to the rod. When the insert has been positioned at least partially in the recess of the expandable head, the upper end of the insert extends beyond the top of the head for, inter alia, preventing a rod from contacting the head of the fastener.

In other preferred embodiments, the insert includes at least one radial projection, and preferably a plurality of radial projections extending outwardly from the periphery of the insert. The radial projections are preferably provided at the upper end of the insert, whereby each projection is sized to extend into one of the slots formed in the expandable head when the insert is at least partially positioned in the recess. The insert has a radial flange preferably located immediately below the radial projections and a socket formed at the upper end thereof. The socket is adapted for receiving a driver, such as a screwdriver, a hexagonal wrench or the like. In this embodiment, the fastener is attached to bone by inserting a driver into the socket of the insert, and then turning the driver to rotate the insert in either a clockwise or counterclockwise direction. In turn, the insert transmits the driving torque from the driver to the fastener. The driving torque is transmitted from the insert to the fastener at the radial projection/slot interface.

In other preferred embodiments the insert does not have a socket, but has an axial bore extending therethrough. In these particular embodiments, the recessed portion of the head has a socket formed therein that is sized to receive the driver. When the insert is positioned at least partially in the recess, the bore extending through the insert is substantially aligned with the socket formed in the head so that a driver can be passed through the bore to reach the socket. The driver is then rotated to rotate the fastener in either a clockwise or counterclockwise direction for anchoring the fastener in the bone.

The coupling element preferably includes a substantially U-shaped element having an upper end and a lower end and a longitudinal axis extending between the upper and lower ends. The coupling element has an interior surface defining a bore extending in a direction substantially parallel to the longitudinal axis thereof and an exterior surface. The interior surface of the coupling element defines the shape of the bore that receives the fastener. In certain embodiments, the bore extends in a direction substantially parallel to the longitudinal axis of the coupling element. The coupling element preferably includes threads adapted for being threadably engaged with the locking element. In one embodiment, the threads are formed on the interior surface of the coupling element and the locking element includes a set screw having external threads for threadably engaging the internal threads of the coupling element. However, in other preferred embodiments, the threads may be formed on the external surface of the coupling element, whereby the locking element includes a locking nut having internal threads adapted for threadably engaging the external surface threads of the coupling element. The coupling element may also have one or more impressions or grooves formed therein for receiving a controlling device, such as a persuader instrument for seating the rod in the coupling element. In some embodiments, the impressions or grooves generally extend in a direction substantially perpendicular to the longitudinal axis of the coupling element.

The interior surface of the coupling element at the lower end thereof preferably defines the seat including a concave portion for receiving the convex portion of the head and allowing the head to pivot relative to the coupling element before being locked in place. The seat is preferably provided adjacent the lower end of the coupling element in an expansion cavity. The expansion cavity preferably has a diameter that is larger than the diameter of the internal threads.

During assembly of the above-mentioned pedicle screw device, the tip end of the fastener is passed through the bore of the coupling element until the expandable head is positioned within the expansion cavity, with the convex outer surface of the head in contact with the concave seat of the coupling element. In certain preferred embodiments, this is accomplished by passing the tip end of the fastener through the upper end of the coupling element toward the lower end thereof. As the tip end and the threaded portion of the fastener passes toward the lower end of the coupling element, the head must be compressed so that it may pass by a small diameter portion of the bore of the coupling element because the outer surface of the head has a diameter that is greater than the smallest diameter of the bore. In one preferred embodiment, the smallest diameter portion of the bore is defined by the internal threads of the coupling element. However, in other embodiments, the smallest diameter portion may be an inwardly extending projection, such as an annular ring. As a result, the flexible arms of the head must flex inwardly for compressing the head, whereupon the head may pass through the small diameter portion of the coupling element. The head continues to pass through the coupling element in a compressed state until the head reaches the expansion cavity, whereupon the flexible arms are free to return to their original, unflexed position.

Once the insert has been positioned in the recess, the flexible arms are incapable of flexing inwardly because the outer dimension of the insert abuts against the inner dimension of the recessed portion of the head. As such, the head can no longer be compressed. Moreover, the fastener cannot be removed from the coupling element as long as the insert remains secured in the recessed portion of the head.

During a spinal fixation operation, after the fastener has been screwed into bone, the coupling element is free to pivot relative to the fastener and the insert secured thereto. The neck portion of the fastener, preferably having a concave surface with a diameter less than the diameter of the threaded portion of the fastener, enables the coupling element to pivot through a broader range of angles relative to the longitudinal axis of the fastener. Thus, a spine rod may be more easily positioned within the rod receiving opening of the coupling element. After the rod has been positioned within the rod receiving opening, the rod is then locked in place by threading the locking element into the threads of the coupling element. As the locking element tightens down upon the rod, the rod, in turn, exerts a downward force on the insert. In turn, the insert moves further into the recess for forcing the flexible arms to move away from one another for expanding the head of the fastener. As the head expands, an increased area of the head engages the seat of the coupling element and the normal force the head exerts on the seat increases. The friction force acting along the interface between the head and the coupling element therefore also increases, since it is proportional to the normal force. The enhanced surface area contact between the head and the coupling element and the higher friction force improve the locking force therebetween and prevents further pivotal movement of the coupling element relative to the fastener. As a result, the likelihood of post-operative shifting and/or moving of the pedicle screw assembly is greatly reduced, thereby minimizing the occurrence of post-operative complications for spinal implant patients. In certain preferred embodiments of the present invention, the coupling element secures the orthopedic rod directly above the head of the fastener. However, in other preferred embodiments, the coupling element may be structured to hold the orthopedic rod offset from the longitudinal axis of the pedicle screw as disclosed in U.S. Pat. No. 5,344,422 to Frigg and U.S. Pat. No. 5,584,831 to McKay.

The present invention also preferably includes a tool for securing the fastener in bone. The tool is preferably a driver having a rotatable shaft and one or more prongs extending from an end of the shaft for engaging the slots. In preferred embodiments the driver has one prong for each slot in the head of the fastener. The driver may also have external threads at a lower end of the shaft. The external threads are preferably adapted for engaging the internal threads of the coupling element when a fastener is being driven into bone. The engagement of the external threads of the driver and the internal threads of the coupling element generally stabilizes the pedicle screw assembly when the fastener is secured to bone. Specifically, the engagement of the threads prevents the coupling element from moving relative to the fastener when driving the fastener into bone, thereby simplifying installation of the fasteners.

These and other objects, features and advantages of the present invention will be more readily apparent from the detailed description of preferred embodiments set forth below, taken in conjunction with the accompanying drawings.

BRIEF DESCRIPTION OF THE DRAWINGS

FIGS. 9B' and 9C' show a pedicle screw assembly, in accordance with another preferred embodiment of the present invention.

DETAILED DESCRIPTION

Figure 1:
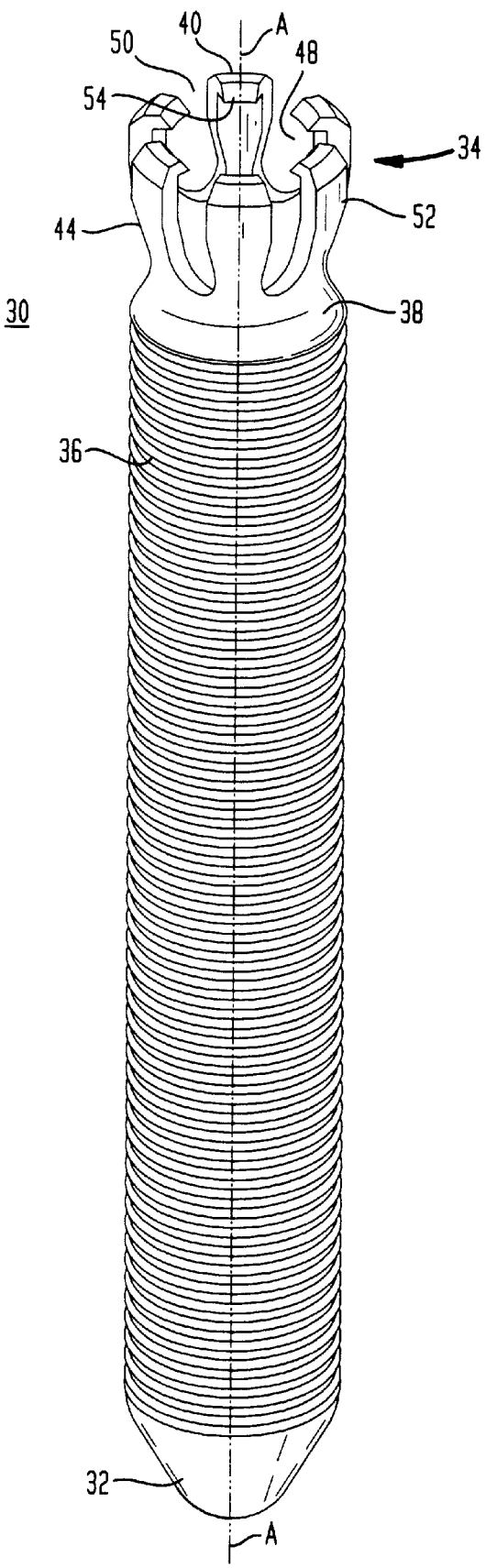
FIG. 1 shows a perspective view of a fastener for a pedicle screw assembly, in accordance with one preferred embodiment of the present invention.

Referring to FIG. 1, in accordance with certain preferred embodiments of the present invention, a slotted head pedicle screw assembly includes a fastener 30 having a tip end 32 for insertion into bone, such as the bone of a vertebral body, and an expandable head 34 at the upper end thereof. The fastener 30 has a longitudinal axis A—A and preferably includes external threads 36 that extend from the tip end 32 of the fastener toward the expandable head 34. The threads 36 terminate at a neck portion 38 of the fastener that is preferably located adjacent the expandable head 34. The external threads 36 have an outer diameter that is greater than a diameter of the neck 38. The neck preferably has a concave surface which enables the fastener 30 to freely pivot through a broader range of angles, as will be described in more detail below. The fastener 30, including the threaded portion 36, the neck 38 and the expandable head 34, are preferably made of a non-organic material that is durable and that can be implanted in a human body, such as titanium or stainless steel.

Figure 2:
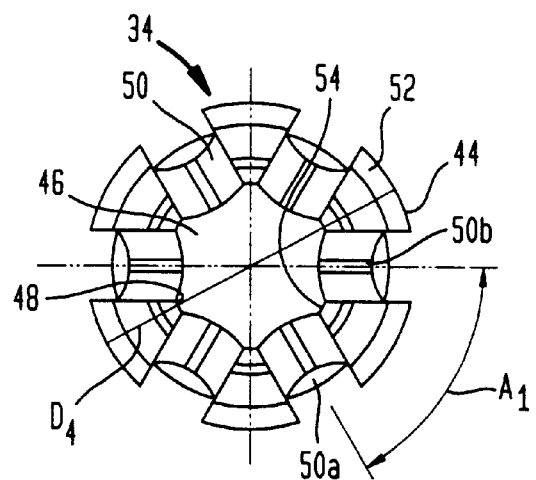
FIG. 2 shows a top view of the fastener shown in FIG. 1.
Figure 3:
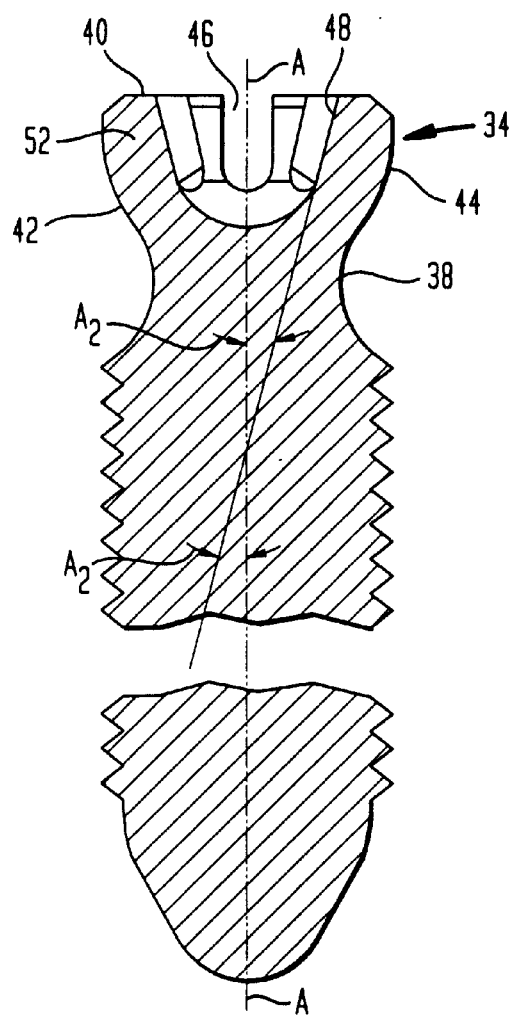
FIG. 3 shows a fragmentary, cross sectional view of the fastener shown in FIG. 1.

Referring to FIGS. 1–3, the expandable head has an upper end 40 remote from the tip 32 and a lower end 42 integrally connected to the neck 38. The outer surface 44 of the head 34 includes a convex portion. The expandable head 34 has a recess 46 formed therein that is preferably centered about the longitudinal axis A—A of the fastener 30. The recess 46 defines an inner surface 48 having an inner dimension. The head 34 also includes a plurality of slots 50 extending between the inner and outer surfaces of the head 34 for allowing expansion and compression of the head, as will be described in more detail below.

Referring to FIGS. 1 and 2, the expandable head 34 of one preferred fastener has six slots 50 extending between the inner and outer surfaces 48, 44 thereof. The slots 50 are generally evenly spaced about the perimeter of the head 34. As shown in FIG. 2, the center of a first slot 50a is displaced from the center of an adjacent second slot 50b by the angle designated $A_1$. In one preferred embodiment, the angle $A_1$ is approximately 60 degrees. Although the FIG. 2 embodiment discloses six slots, it is contemplated that any number of slots, including just one slot, may be formed in the head. The slots 50 subdivide the expandable head 34 into a plurality of flexible arms 52, whereby each flexible arm includes a lower end integrally connected to the fastener adjacent the neck portion thereof and an upper end remote therefrom. As shown in FIG. 2, the flexible arms 52 generally surround the recess 46 and are preferably in an evenly-spaced configuration around the perimeter of the recess 46. Each flexible arm 52 includes a tab 54 at an upper end thereof that extends from the arm toward the longitudinal axis A—A in the center of the recess 46. As shown in FIG. 3, the inner surface 48 of the recess 46 defines an angle $A_2$ with the longitudinal axis A—A of the fastener 30. In one embodiment, the angle $A_2$ is approximately 15 degrees.

Figure 4A:
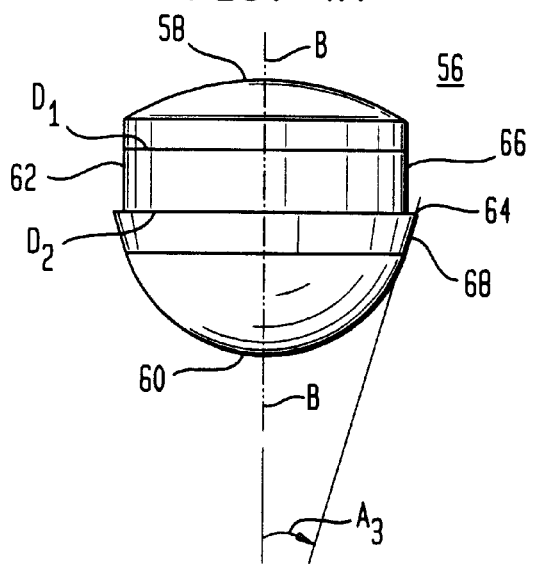
FIG. 4A shows a side view of an insert for a pedicle screw assembly, in accordance with one preferred embodiment of the present invention.
Figure 4B:
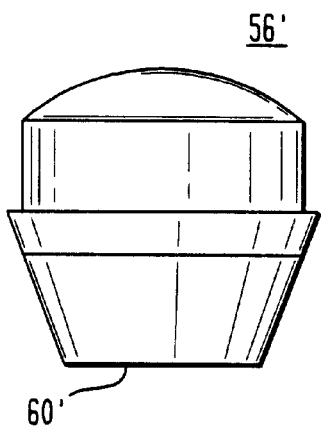
FIG. 4B shows a side view of an insert for a pedicle screw assembly, in accordance with further preferred embodiments of the present invention.
Figure 5:
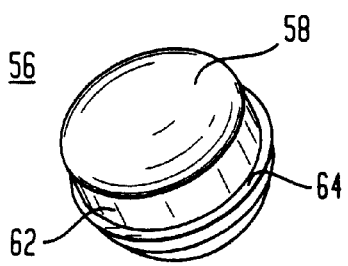
FIG. 5 shows a perspective view of the insert shown in FIG. 4.
Figure 6:
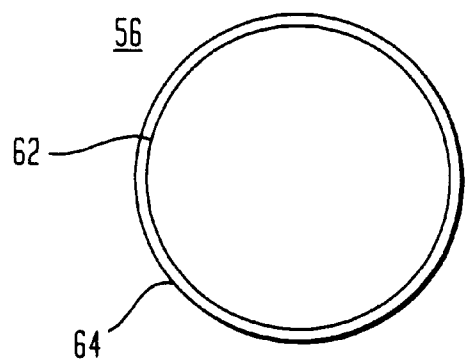
FIG. 6 shows a top view of the insert shown in FIG. 4.

Referring to FIGS. 4A, 5 and 6, the pedicle screw assembly of the present invention also includes an insert 56 that may be positioned and/or secured at least partially within the recess of the expandable head (FIG. 2). As shown in FIG. 4, the insert 56 has an upper end 58 with a radial surface, a lower end 60 with a radial surface and an outer surface 62 that extends between the upper and lower ends 58, 60 thereof. The insert 56 has a longitudinal axis designated B—B extending between the upper and lower ends and also includes a flange 64 extending around the largest diameter section of the outer surface 62. In other words, the flange 64 defines the largest outer dimension of the insert 56. However, in other preferred embodiments, the flange does not define the largest outer dimension of the insert 56.

Referring to FIGS. 4A, 5 and 6, the pedicle screw assembly of the present invention also includes an insert 56 that may be positioned and/or secured at least partially within the recess of the expandable head (FIG. 2). As shown in FIG. 4A, the insert 56 has an upper end 58 with a radial surface, a lower end 60 with a radial surface and an outer surface 62 that extends between the upper and lower ends 58, 60 thereof. The insert 56 has a longitudinal axis designated B-B extending between the upper and lower ends and also includes a flange 64 extending around the largest diameter section of the outer surface 62. In other words, the flange 64 defines the largest outer dimension of the insert 56. However, in other preferred embodiments, the flange does not define the largest outer dimension of the insert 56.

The outer surface 62 of the insert has a first section 66 with a first diameter designated $D_1$. The first section 66 extends between the upper end 58 of the insert 56 and the flange 64. The outer surface of the insert 56 has a second section 68 extending between the flange 64 and the lower end 60 of the insert 56. The outer dimension of the insert 56 at the flange 64 has a second diameter designated $D_2$ that is greater than $D_1$. Between the flange 64 and the lower end 60 of the insert, the outer surface 62 tapers inwardly relative to the longitudinal axis B—B of the insert at an angle designated A3. Referring to FIGS. 3 and 4A, it is preferable that angle A3 of insert 56 is greater than angle A2 of the recess 46 so that the insert is able to expand the outer dimension 44 of the head 34 for reasons that will be set forth in further detail below. Although the insert shown in FIG. 4A has a substantially spherically-shaped lower end, it is contemplated that the lower end 60' of the insert 56' may be substantially flat as shown in FIG. 4B.

Figure 7:
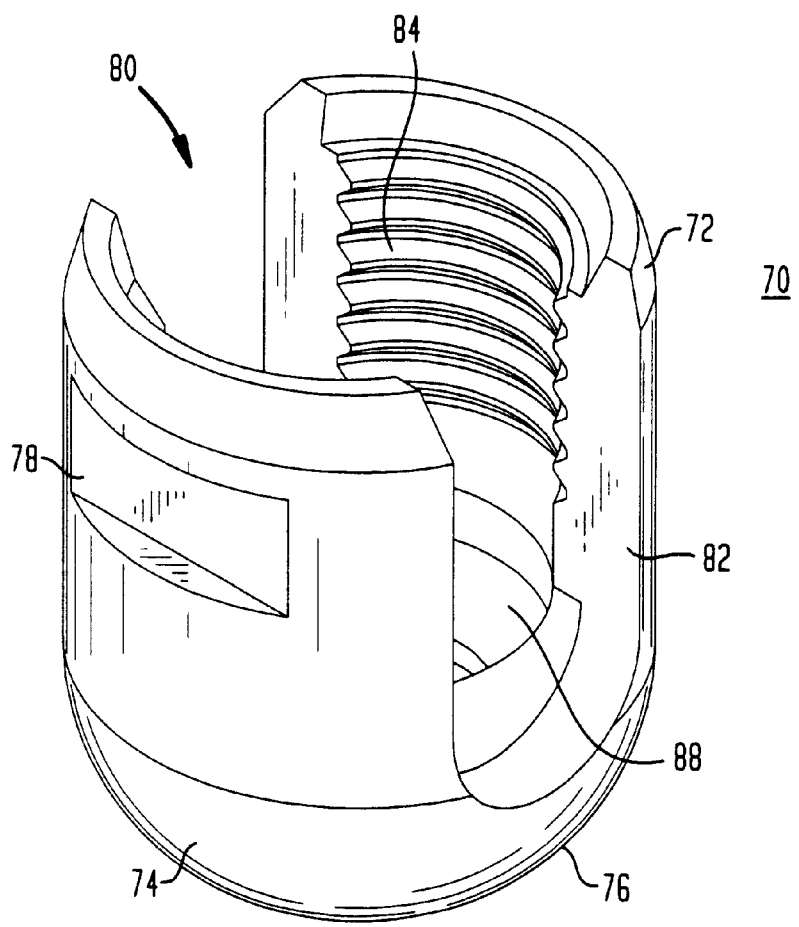
FIG. 7 shows a perspective view of a coupling element for a pedicle screw assembly, in accordance with one preferred embodiment of the present invention.
Figure 8:
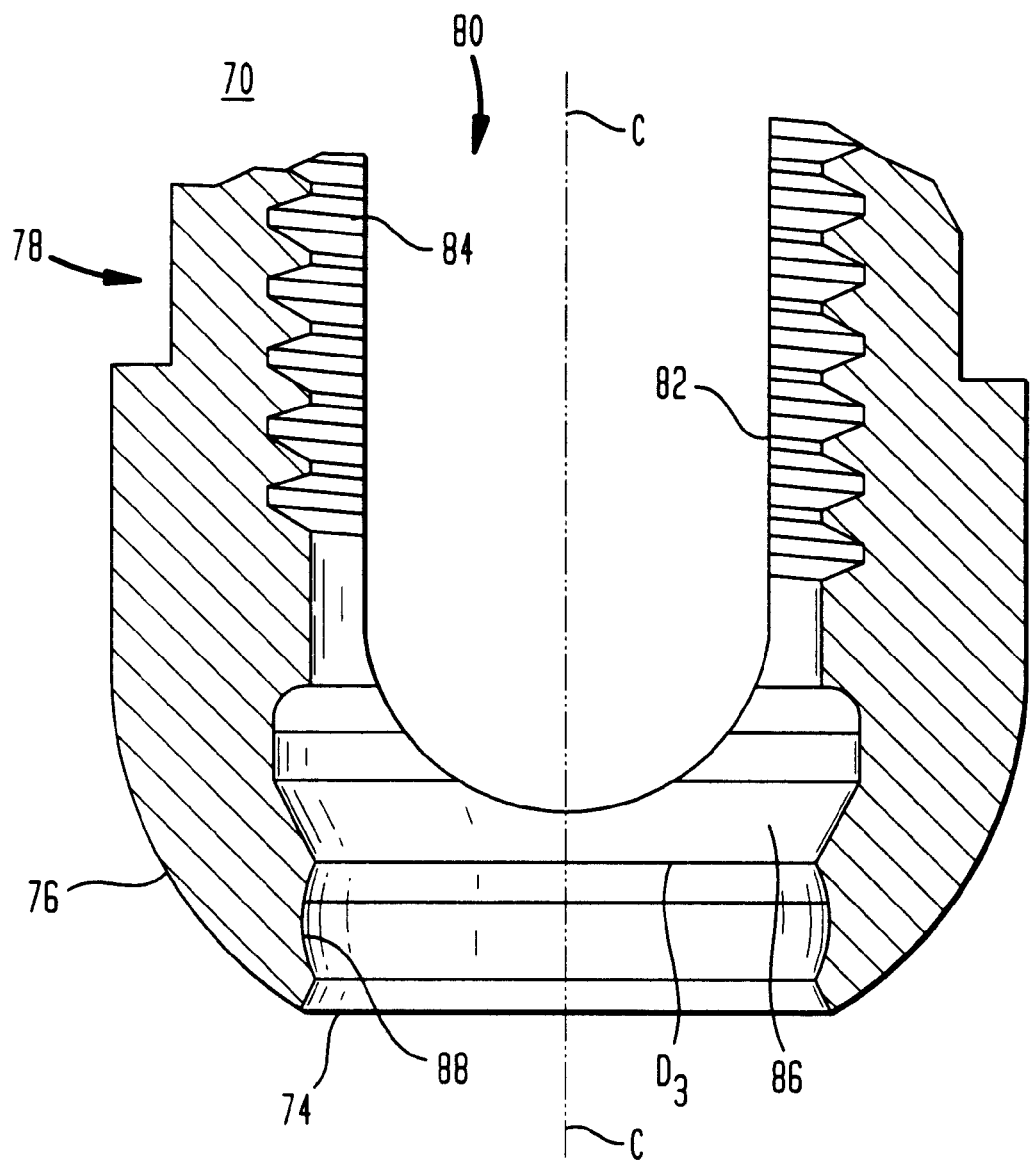
FIG. 8 shows a fragmentary, cross-sectional view of the coupling element shown in FIG. 7.

Referring to FIGS. 7 and 8, the pedicle screw assembly also includes a coupling element 70 for coupling an orthopedic rod with the fastener 30 (FIG. 1). The coupling element 70 has an upper end 72 and a lower end 74, and a longitudinal axis designated C—C extending from the upper to the lower end. The coupling element 70 also has an outer surface 76 including a convex portion at the lower end 74 thereof. The outer surface also preferably includes grooves 78 formed therein so that the coupling element may be grasped and/or maneuvered using a securing element or tool, such as a persuader instrument used to seat the orthopedic rod in the pedicle screw assembly. The grooves 78 preferably extend in directions substantially perpendicular to the longitudinal axis C—C of the coupling element.

A bore 80 extends along the longitudinal axis C—C of the coupling element 70 for receiving the fastener. The bore 80 defines an inner surface 82 of the coupling element having internal threads 84 adjacent the upper end 72 and an expansion cavity 86 adjacent the lower end 74. The lower end of the expansion cavity 86 preferably has a seat 88 with a concave surface for receiving the convex-shaped outer surface of the expandable head (FIG. 1). The inner dimension D3 of the expansion cavity 86 has a diameter that is greater than the outer dimension of the outer surface of the expandable head (FIG. 2), when the head is in a normal, unexpanded state. As a result, the fastener and the coupling element are able to rotate and pivot freely relative to one another when the head is unexpanded, as will be described in more detail below.

Figure 9D:
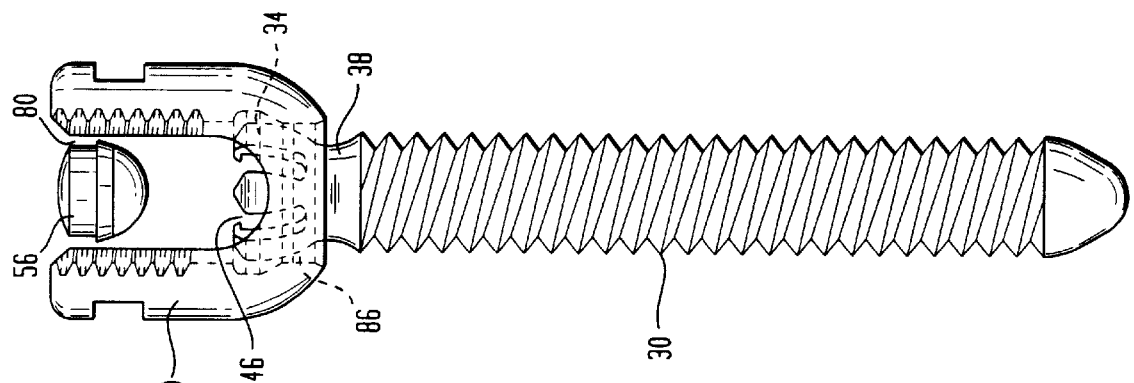
FIG. 9D shows the subassembly of FIGS. 9A–9C during a further step in the assembly process.
Figure 9A:
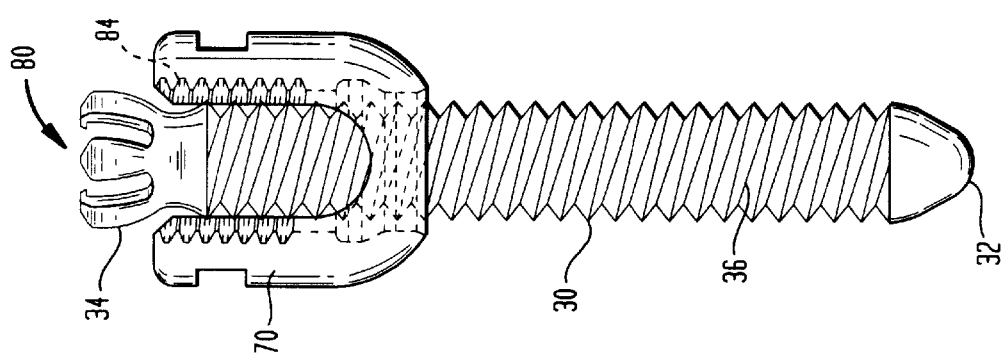
FIG. 9A shows a method of assembling a pedicle screw assembly whereby the fastener of FIG. 1 is assembled with the coupling element of FIG. 7, in accordance with one preferred embodiment of the present invention.

FIGS. 9A–9E show one preferred method for assembling a slotted head pedicle screw assembly. Referring to FIG. 9A, the tip end 32 of the fastener 30 is passed through the bore 80 (FIG. 8) of the coupling element 70, at the upper end of the coupling element. The threaded portion 36 of the fastener 30 is able to pass freely through the bore because the external diameter of the threads 36 is less than the diameter of the internal threads 84 of the coupling element. However, once the head 34 reaches the internal threads 84, the fastener 30 can no longer pass freely through the bore 80 because the outer diameter of the head 34 is greater than the diameter of the internal threads 84.

Figure 9B:
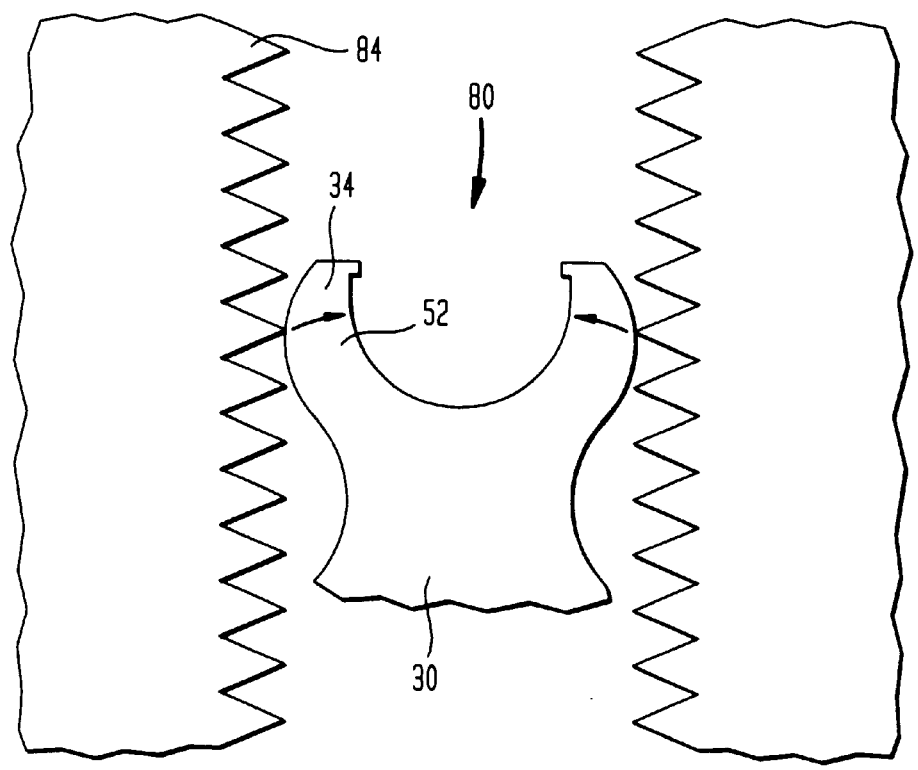
FIG. 9B shows a fragmentary view of the subassembly of FIG. 9A during a further step in the assembly process.
Figure 9C:
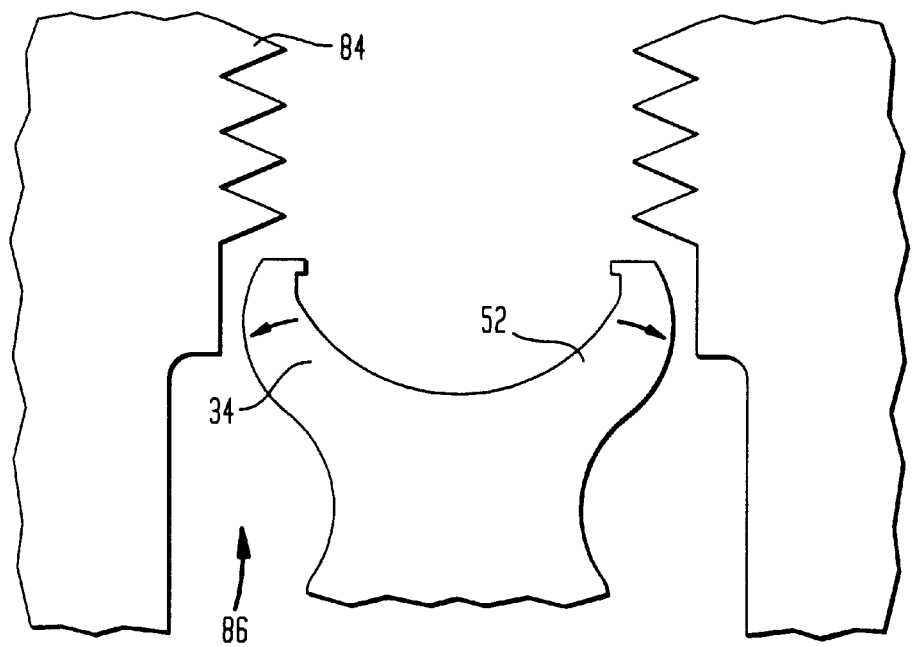
FIG. 9C shows the subassembly of FIG. 9B during a further step in the assembly process.
Figure 9B:
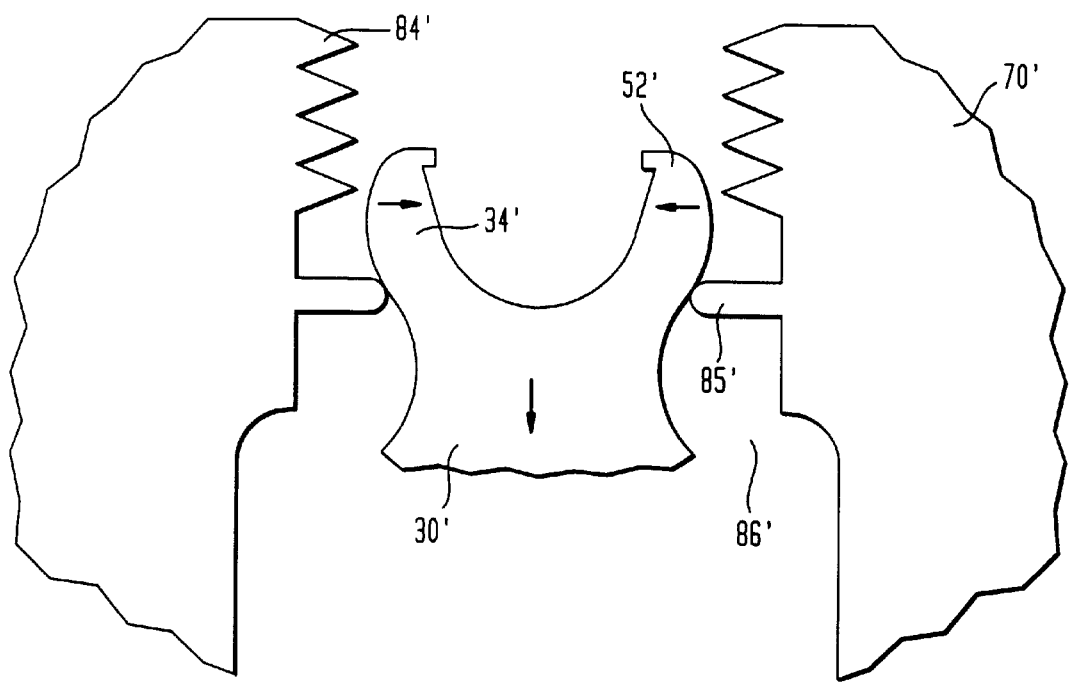
Figure 9C:
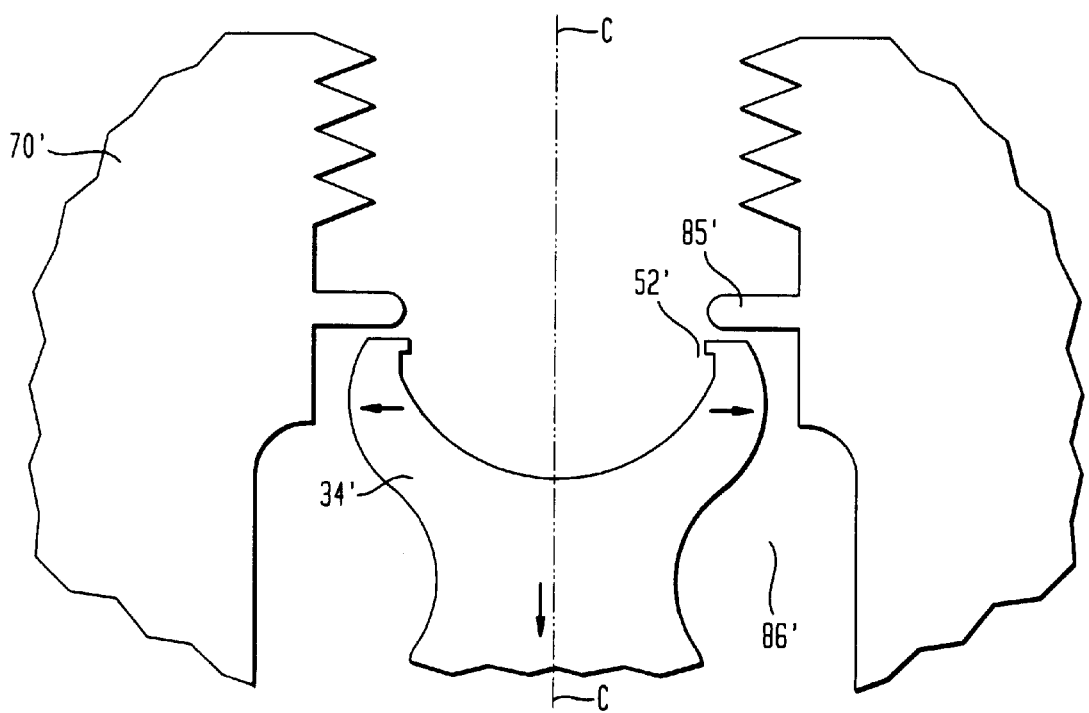

Referring to FIG. 9B, in order to continue moving the head 34 of the fastener 30 through the bore 80 and toward the lower end of the coupling element, the flexible arms 52 of the head must flex inwardly toward one another, in the direction indicated by the arrows, for compressing the head. Upon being compressed, the outer diameter of the head 34 is less than or equal to the diameter of the internal threads 84 of the coupling element. Referring to FIG. 9C, once the head 34 moves past the internal threads 84 and into the expansion cavity 86, the flexible arms 52 are free to move away from one another in the direction indicated by the arrows. The flexible arms are free to return to their original orientation because the inner diameter of the expansion cavity is greater than the outer diameter of the head when the head is in an uncompressed state.

Referring to FIGS. 9B' and 9C', in other preferred embodiments, the outer diameter of the head 34' is less than the diameter of the internal threads 84' of the coupling element 70'. As a result, the head 34' is able to pass freely by the internal threads 84'. In these embodiments, the bore has a minimum diameter section 85' located between the internal threads 84' and the expansion cavity 86' of the coupling element 70'. As shown in FIG. 9B', the flexible arms 52' of the head 34' must move inwardly toward one another for compressing the head. Upon being compressed, the outer diameter of the head 34' is less than or equal to the diameter of the minimum diameter section 85' of the coupling element 70'. Referring to FIG. 9C', once the head 34' moves past the minimum diameter section 85' and into the expansion cavity 86', the flexible arms 52' are free to move away from one another for returning the head 34' to its original, uncompressed state. The minimum diameter portion may be a flange 85' projecting inwardly toward the central axis C—C of the coupling element 70'.

FIG. 9D shows the fastener 30 and the coupling element 70 after the expandable head 34 has been positioned in the expansion cavity 86 of the coupling element. Because the outer surface of the expandable head 34 has a diameter which is smaller than the inner diameter of the expansion cavity 86, the expandable head 34 and the fastener 30 are free to pivot relative to the coupling element 70. The reduced diameter neck 38 enables the fastener 30 to pivot over a broader range of angles relative to the coupling element 70'. Insert 56 (FIG. 4A) is then positioned at least partially in the recess 46 of the expandable head 34.

Figure 10A:
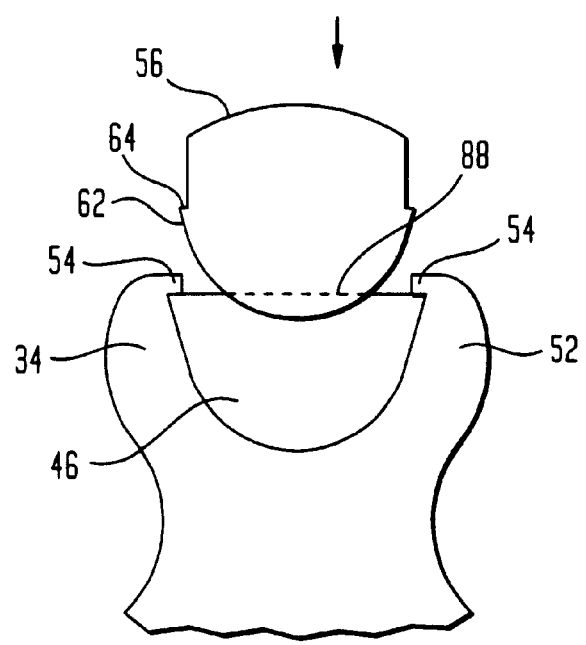
FIGS. 10A–10C show one method for assembling the insert of FIG. 4A with the fastener of FIG. 1, in accordance with certain preferred embodiments of the present invention.
Figure 10B:
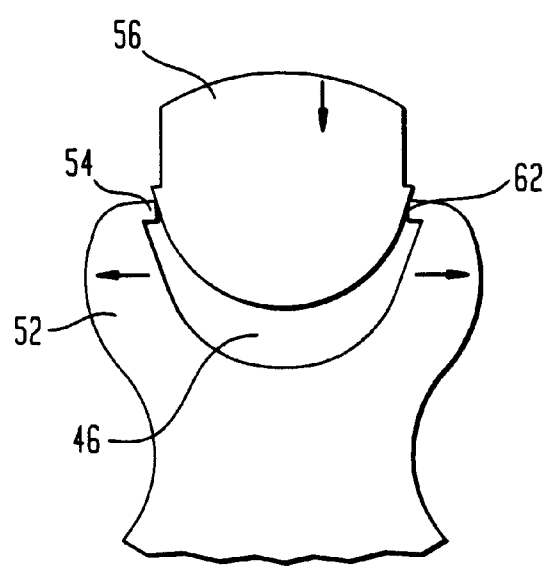
Figure 10C:
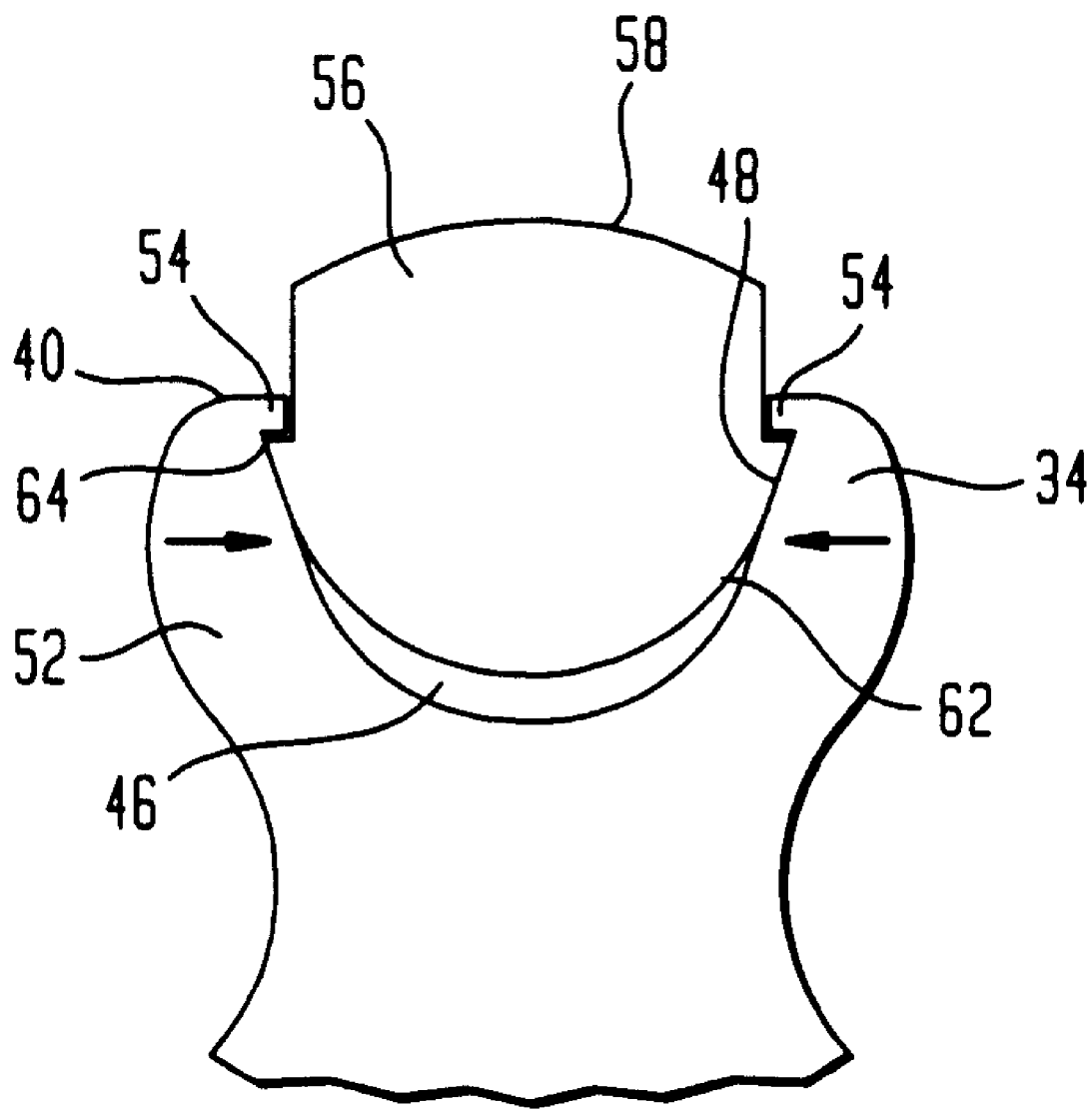

FIGS. 10A–10C show one preferred method for providing the insert 56 at least partially in the recess 46. FIG. 10A shows the insert 56 adjacent the recess 46 of the head 34 before the outer surface of the insert 62 engages the flexible arms 52 of the head. The outer dimension of the insert at the flange 64 is greater that the inner dimension of the recess. The inner dimension 88 of the recess extends between opposed tabs 54 at the upper ends of the flexible arms 52.

In FIG. 10B, the insert 56 is abutted against the tabs 54 of the flexible arms 52 and moved in a downward direction into the recess 46. As a result, the outer surface 62 of the insert engages tabs 54 for forcing the flexible arms 52 away from one another in the directions indicated by the arrows. Referring to FIG. 10C, the flexible arms 52 continue to flex away from one another until the flange 64 of the insert 56 passes the tabs 54, whereupon the flexible arms 52 are free to move back toward one another in the directions indicated by the arrows. The tabs 54 then hold the insert 56 secured at least partially in the recess 46. Upon being secured in the recess, the upper end 58 of the insert 56 is preferably above the top 40 of the head 34 for reasons that will be set forth in more detail below. Once the insert 56 has been secured by the tabs 54, the flexible arms 52 are no longer capable of compressing inwardly toward one another because the outer surface 62 of the insert is in close engagement with the inner surface 48 of the flexible arms 52, i.e. the inner surface of the recess 46. As a result, once the insert 56 has been secured in the recess 46, it is very difficult to remove the insert from the recess without significantly manipulating the flexible arms 52 of the expandable head.

Figure 11:
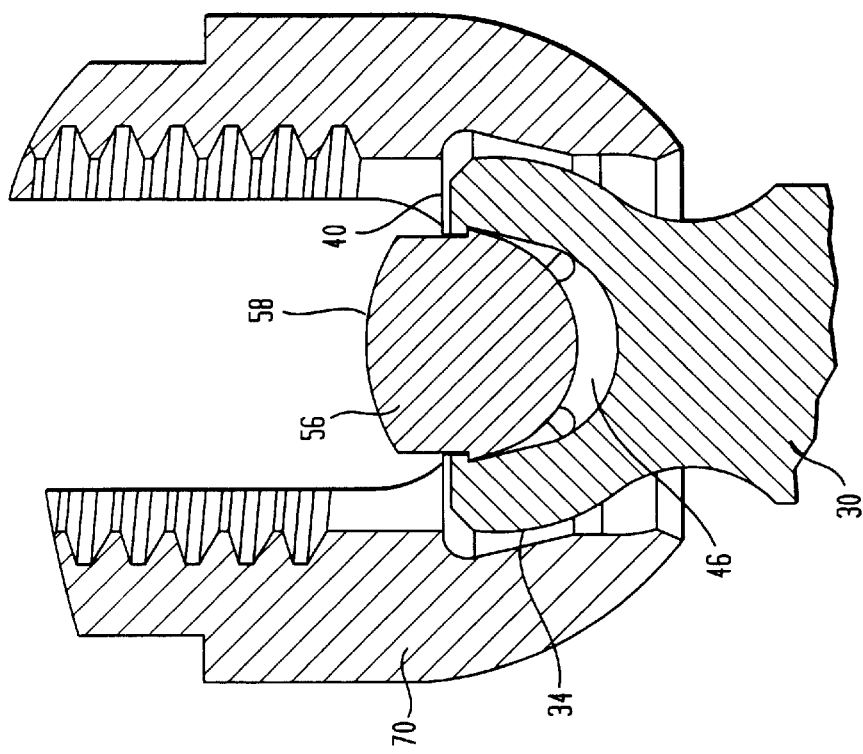
FIG. 11 shows a fragmentary, cross-sectional view of the pedicle screw assembly shown in FIG. 9E.
Figure 9E:
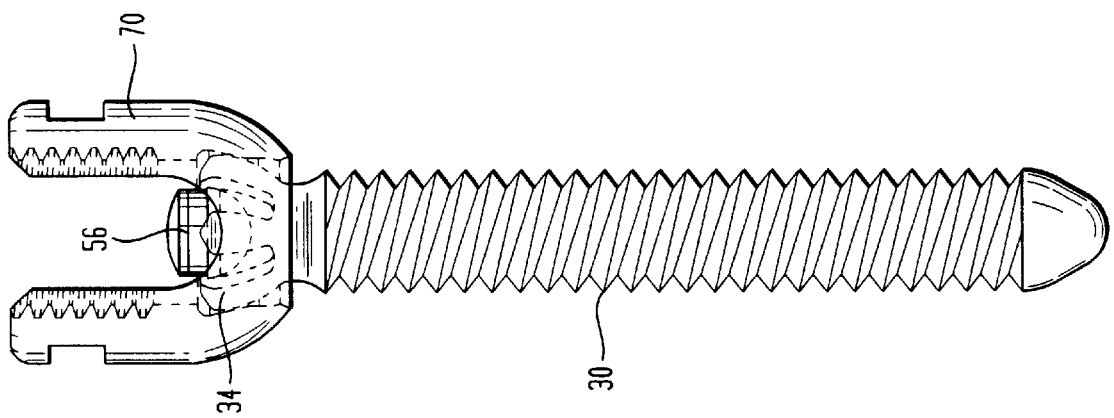
FIG. 9E shows the subassembly of FIG. 9D during yet a further step, in the assembly process.

Referring to FIGS. 9E and 11, once the insert 56 has been secured in the recess 46, the insert 56 and the fastener 30 are able to pivot together freely relative to the coupling element 70. As shown in FIG. 11, the insert 56 is preferably not completely secured within the recess 46 and desirably has a relatively high profile with respect to the upper end 40 of the expandable head 34. As a result, the upper end 58 of the insert 56 sits above the upper end 40 of the fastener 30 for preventing an orthopedic rod (not shown) positioned within the coupling element from contacting the head 34.

Figure 12:
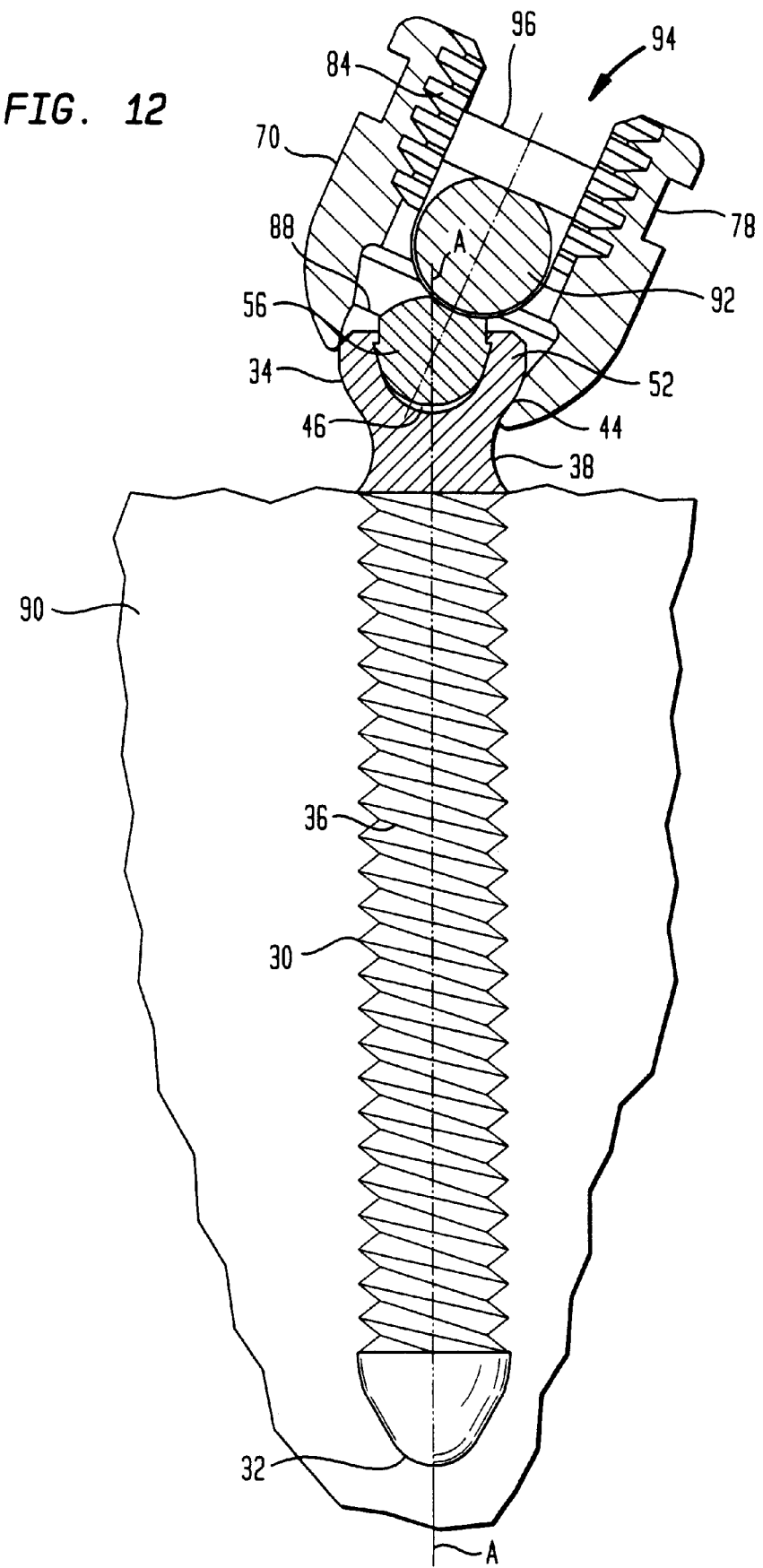
FIG. 12 shows a side view of the pedicle screw assembly of FIG. 9E with an orthopedic rod secured in a rod receiving opening of the coupling element, in accordance with one preferred embodiment of the present invention.

Referring to FIG. 12, after the insert 56 has been secured within the recess 46 of the expandable head 34, the pedicle screw assembly is ready to be inserted into bone 90. In a first step, the fastener 30 may be anchored to bone 90 by drilling a pilot hole into the bone. The tip end 32 of the fastener 30 is then placed in the pilot hole and the fastener is screwed into the bone using a driver or tool. The driver may be a screwdriver or may include one or more projections extending therefrom designed to fit within the one or more slots formed in the head, as will be described in more detail below. The threaded fastener 30 is driven into the bone 90 until a sufficient portion of the fastener is anchored in the bone.

After the fastener 30 is anchored in the bone 90, the coupling element 70 is free to pivot and rotate relative to the fastener. This pivoting and/or rotary action may be necessary so that an orthopedic rod 92 may be positioned within the rod receiving opening 94 of the coupling element 70. The rod receiving opening is preferably defined by a U-shaped opening at the top of the coupling element. As mentioned above, the neck 38 of the fastener 30 has a concave surface and a diameter that is smaller than the diameter of the threaded portion 36 of the fastener. As a result, the coupling element 70 is able to pivot over a broader range of angles relative to the longitudinal axis A—A of the fastener 30 than would be possible if the threads extended all the way to the lower end of the head 34. The coupling element 70 may then be pivoted and/or rotated so that the orthopedic rod 92 can be positioned in the rod receiving opening 94. The coupling element may be moved using grooves 78 or by grasping the body of the coupling element.

After the rod 92 has been positioned, a set screw 96 having external threads is threaded into the internal threads 84 of the coupling element 70. The set screw 96 continues to be threaded in the internal threads 84 until the set screw abuts against the rod 92. The set screw 96 is then further rotated into the internal threads for locking the rod 92 in the rod receiving channel 94. The set screw 96 applies a downward force on the rod 92, which, in turn, applies a downward force upon the insert 56. The downward force on the insert 56, in turn, moves the insert further into the recess 46 for wedging the flexible arms 52 away from one another and expanding the outer dimension of the head. The set screw 96 continues to be tightened until the outer surface 44 of the expandable head 34 contacts the seat 88 of the coupling element 70 for locking the coupling element in place and preventing further pivotal movement of the coupling element relative to the fastener. The expandable nature of the head provides for a greater level of surface area contact between the head and the coupling element than is possible with fasteners having rigid heads. The expandable heads provides for more friction force between the head and the seat of the coupling element so that the locking force generated is significantly greater.

Figure 13:
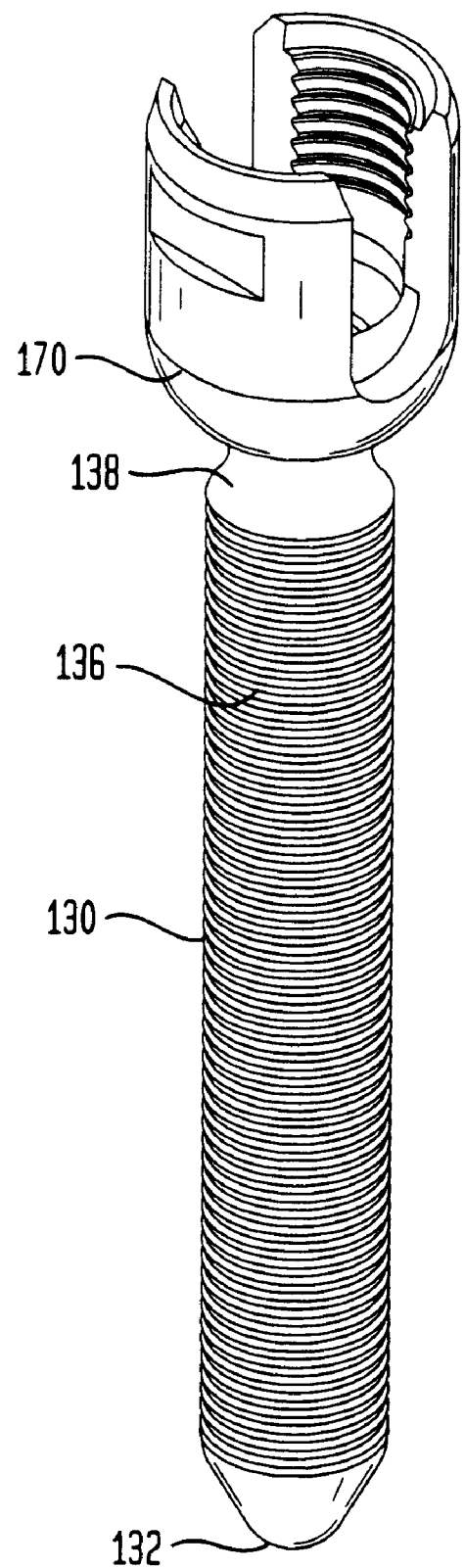
FIG. 13 shows a pedicle screw assembly, in accordance with further preferred embodiments of the present invention.

FIGS. 13–19 show a slotted head pedicle screw assembly in accordance with further preferred embodiments of the present invention. FIG. 13 shows a threaded fastener 130 including a tip end 132, a threaded portion 136, a neck 138 and an expandable head having a recess and slots for dividing the head into flexible arms. The assembly also includes a coupling element 170. The fastener 130 and the coupling element 170 are substantially similar to that described above in respective FIGS. 1 and 7.

Figure 14A:
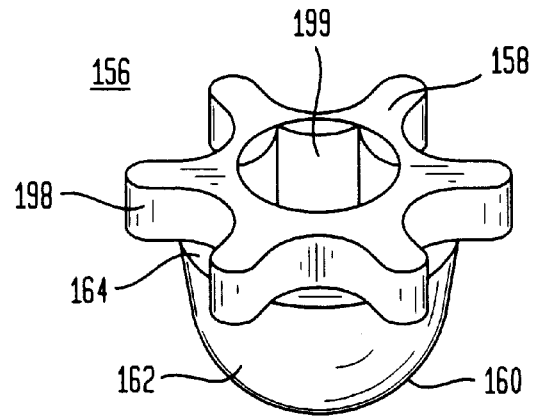
FIG. 14A shows a perspective view of an insert used in the pedicle screw assembly shown in FIG. 13.
Figure 14B:
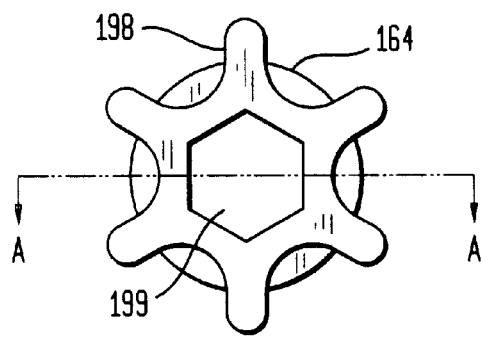
FIG. 14B shows a top view of the insert shown in FIG. 14A.
Figure 14C:
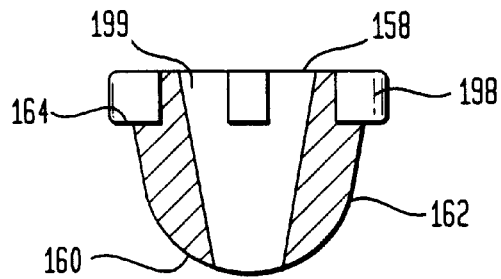
FIG. 14C shows a cross-sectional view of the insert of FIG. 14B along line A—A.

Referring to FIGS. 14A–14C, an insert 156 for the assembly has an upper end 158, a lower end 160 with a radial surface and an outer surface 162 that extends between the upper and lower ends thereof. The upper end 158 of the insert 156 has radial projections 198 extending outwardly therefrom. The radial projections 198 are sized for fitting within the slots formed in the expandable head (FIG. 1). The insert includes a socket 199 formed at the upper end thereof for receiving a driver, such as a hexagonal wrench or a screwdriver. The insert also includes a flange 164 provided immediately below the projections. The flange extends around the largest diameter section of the outer surface 162, and preferably defines the outer dimension of the insert. The outer surface of the insert tapers inwardly at an angle relative to the longitudinal axis of the insert so that the insert is able to force the flexible arms of the head away from one another as the insert moves further into the recess of the head.

Figure 16:
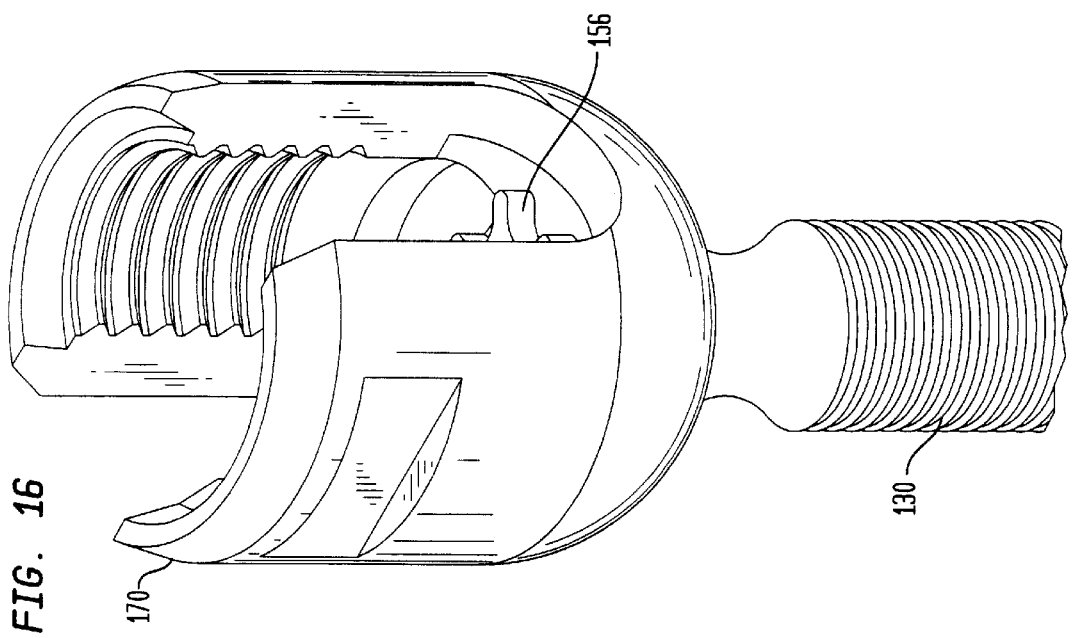
FIG. 16 shows another fragmentary perspective view of the pedicle screw assembly shown in FIG. 13.
Figure 15:
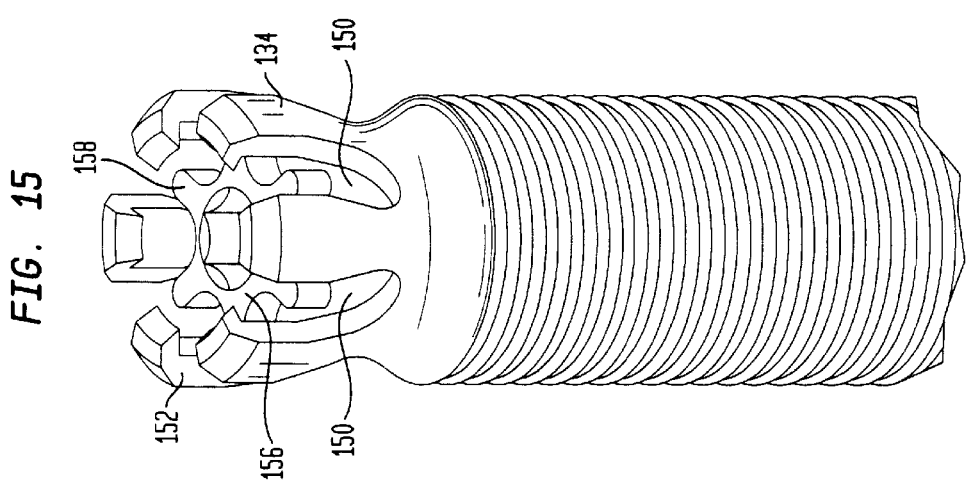
FIG. 15 shows a fragmentary perspective view of the pedicle screw assembly shown in FIG. 13.

FIG. 15 shows a fragmentary view of the assembly with the insert 156 of FIG. 14A secured within the recess of the expandable head 134. The insert is secured within the recess using a process that is generally similar to that described above in FIGS. 10A–10C. The radial projections 198 extending from the upper end 158 of the insert are disposed within the slots 150 of the head. The flexible arms 152 of the head are prevented from flexing inwardly toward one another by the insert 156. In certain embodiments, the outer surface 162 (FIG. 14C) of the insert may prevent the flexible arms from flexing inwardly toward one another. Referring to FIG. 16, after the insert 156 has been secured to the head of the fastener 130, the fastener and insert are free to pivot together relative to the coupling element 170.

Figure 18:
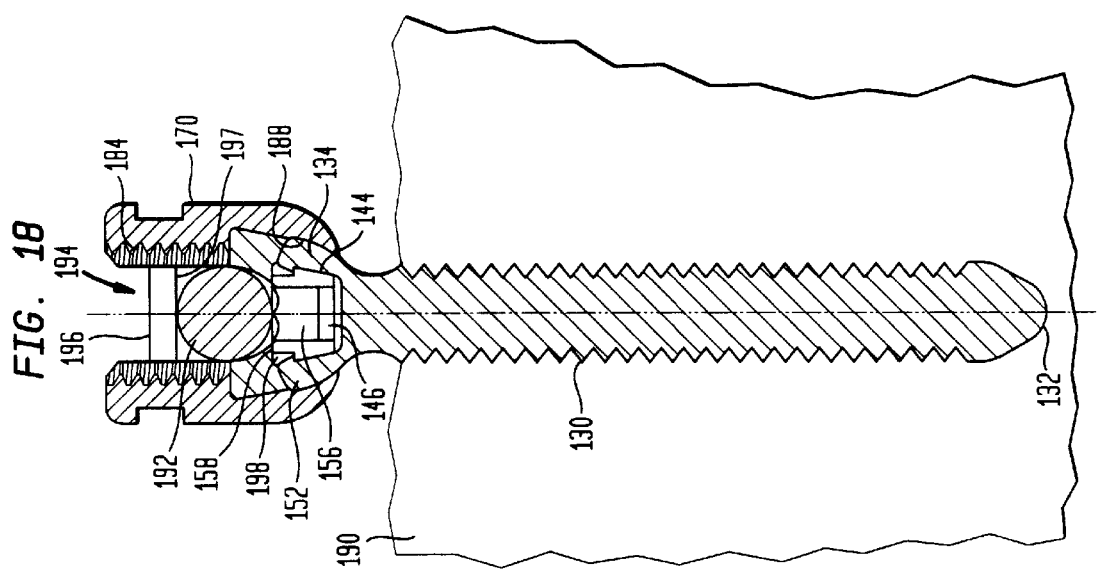
FIG. 18 shows a cross-sectional side view of the pedicle screw assembly shown in FIGS. 13 and 17 after the fastener has been anchored in bone and an orthopedic rod has been secured within a rod receiving opening of the coupling element.
Figure 17:
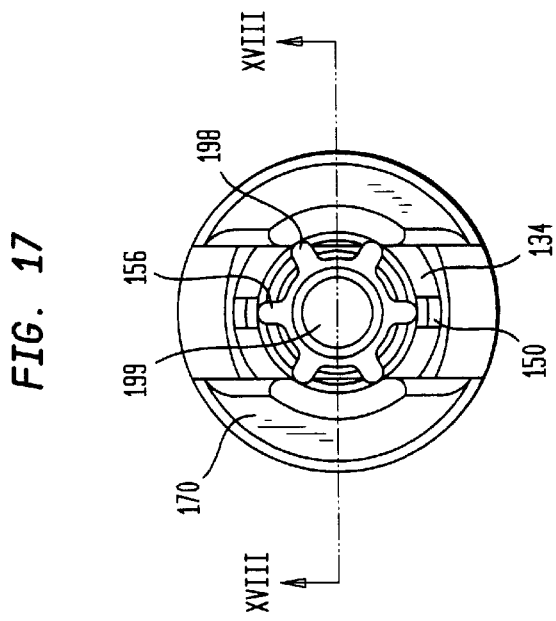
FIG. 17 shows a top view of the pedicle screw assembly shown in FIG. 13.

Referring to FIGS. 17 and 18, the fastener may be secured to a bone 190 by first drilling a pilot hole into the bone and then inserting the tip end 132 of the fastener into the pilot hole. A driver, such as a hexagonal wrench, is then inserted into the socket 199 formed at the upper end of the insert 156. As the driver rotates the insert 156, the radial projections 158 of the insert 156 engage the flexible arms of the head 134 for driving the fastener into the bone 190. After the fastener is anchored in bone 190, the coupling element is free to pivot and rotate relative to the fastener so that an orthopedic rod 192 may be positioned within the rod-receiving opening 194 of the coupling element 170. After the rod 192 is positioned, an externally threaded locking member 196 is threadably engaged with the internal threads 184 of the coupling element 170 and driven toward the rod 192 until a lower end 197 of the locking member 196 engages the orthopedic rod 192. The locking member 196 continues to be driven into the internal threads 184 for providing a downward force upon the orthopedic rod 192. In turn, the orthopedic rod 192 provides a downward force upon the upper end 158 of the insert 156 for forcing the insert 156 further into the recess 146 of the expandable head 134. As the insert moves further into the recess of the expandable head, the outer surface 144 of the insert forces the flexible arms 152 to move away from one another for expanding the outer diameter of the expandable head. As a result, the outer surface of the expandable head engages the seat 188 of the coupling element 170 for locking the coupling element in place relative to the fastener 130 and preventing further pivotal movement of the coupling element relative to the fastener.

FIGS. 19A–23 show an insert 256 for a pedicle screw assembly in accordance with still further preferred embodiments of the present invention. In this particular embodiment, the fastener 230 and coupling element 270 are substantially similar in design to the embodiments shown above. However, referring to FIGS. 19A and 19B, the insert 256 has an outer surface that is substantially spherical in shape and has a minimum diameter section 264 at a top 258 thereof. The spherical shape of the outer surface 262 of the insert 256 allows the insert to rotate freely within the recess 246 of the head 234 of the fastener 230.

Figure 19A:
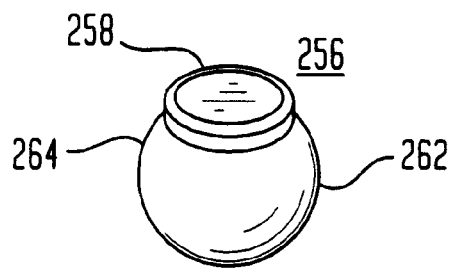
FIG. 19A shows a perspective view of an insert for a pedicle screw assembly, in accordance with further preferred embodiments of the present invention.
Figure 19B:
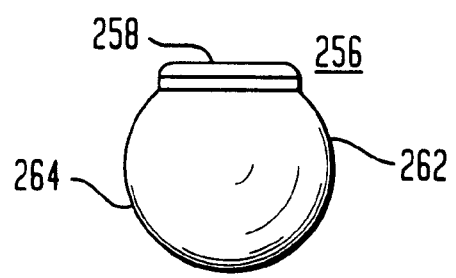
FIG. 19B shows a side view of the insert shown in FIG. 19A.
Figure 20C:
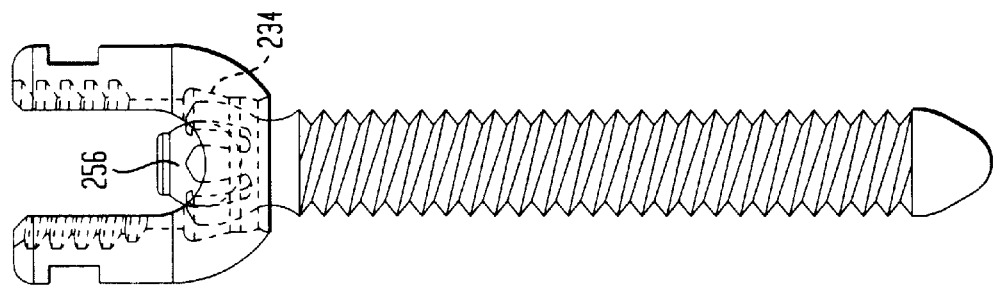
FIGS. 20A–20C show a method of assembling a pedicle screw assembly using the insert shown in FIG. 19A.
Figure 20B:
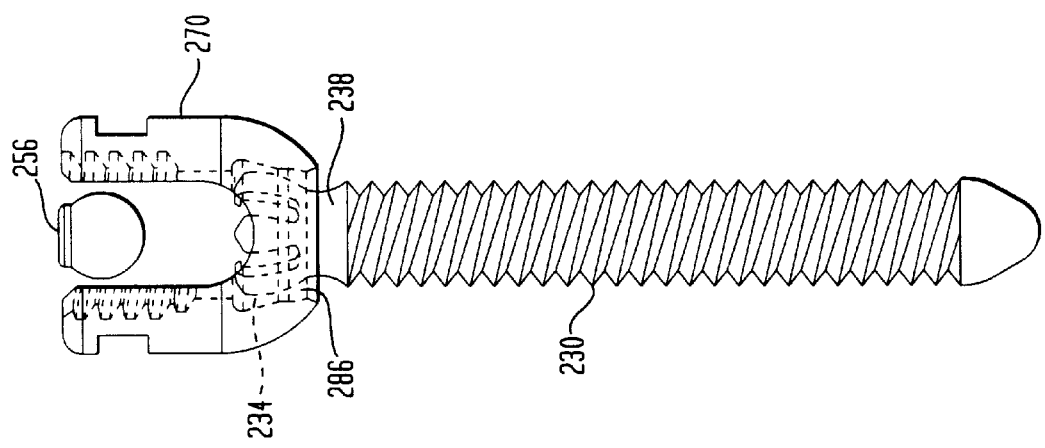
Figure 20A:
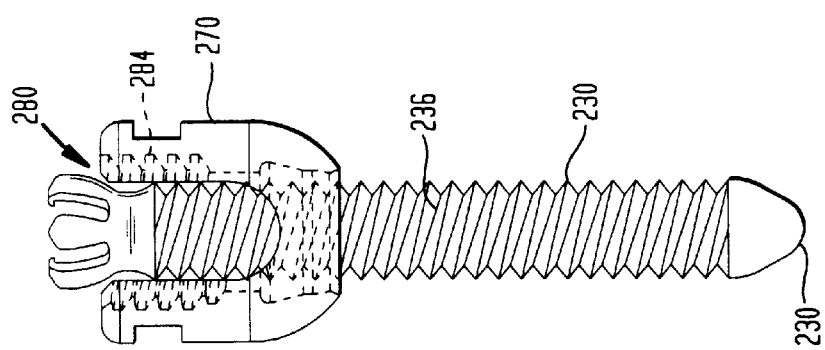

FIGS. 20A–20C show a preferred method for assembling a slotted head pedicle screw assembly using the insert 256 of FIGS. 19A and 19B. Referring to FIG. 20A, the tip end 232 of the fastener 230 is passed through the bore 280 of the coupling element 270. The threaded portion 236 of the fastener 230 is able to pass freely through the bore 280 because the external diameter of the threads 236 is less than the minimum diameter of the bore 280 of the coupling element 270. As set forth above, the minimum diameter of the bore can be defined by either the internal threads 284 of the coupling element 270 or another feature designed into the bore of the coupling element, such as a flange (e.g., item 85' in FIG. 9B'). However, once the head 234 reaches the minimum diameter section of the coupling element 270, the fastener 230 can no longer pass freely through the bore 280 because the outer diameter of the head 224 is greater than the minimum diameter.

FIG. 20B shows the fastener 230 and the coupling element 270 after the expandable head 234 has been positioned in the expansion cavity 286 of the coupling element 270. Because the outer surface of the expandable head 234 has a diameter which is smaller than the inner diameter of the expansion cavity 286, the expandable head 234 and the fastener 230 are free to pivot relative to the coupling element 270. The reduced diameter neck portion 238 of the fastener enables the fastener 230 and the coupling element 70 to pivot over a broader range of angles relative to one another.

Figure 21:
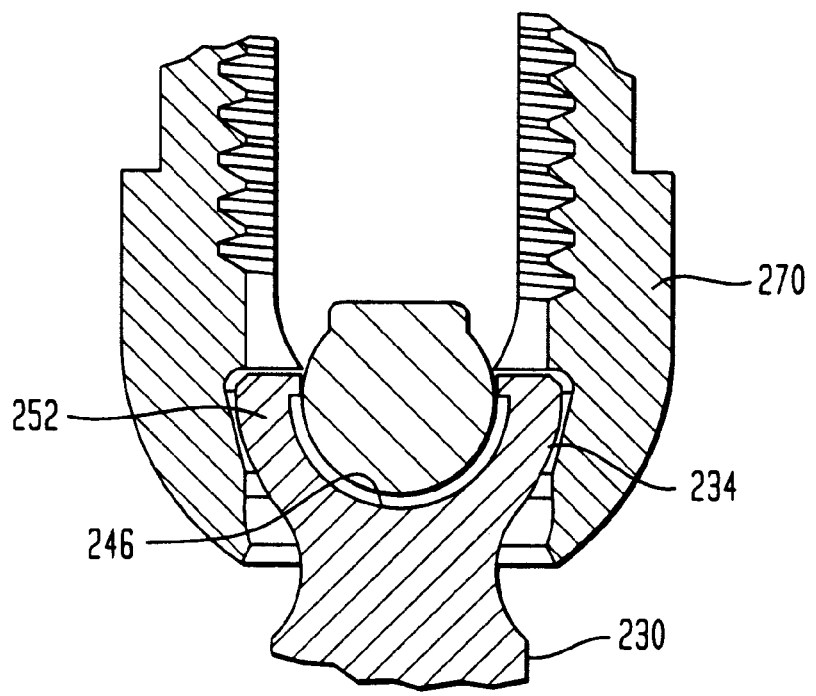
FIG. 21 shows an enlarged fragmentary cross-sectional view of the pedicle screw assembly shown in FIG. 20C.
Figure 22:
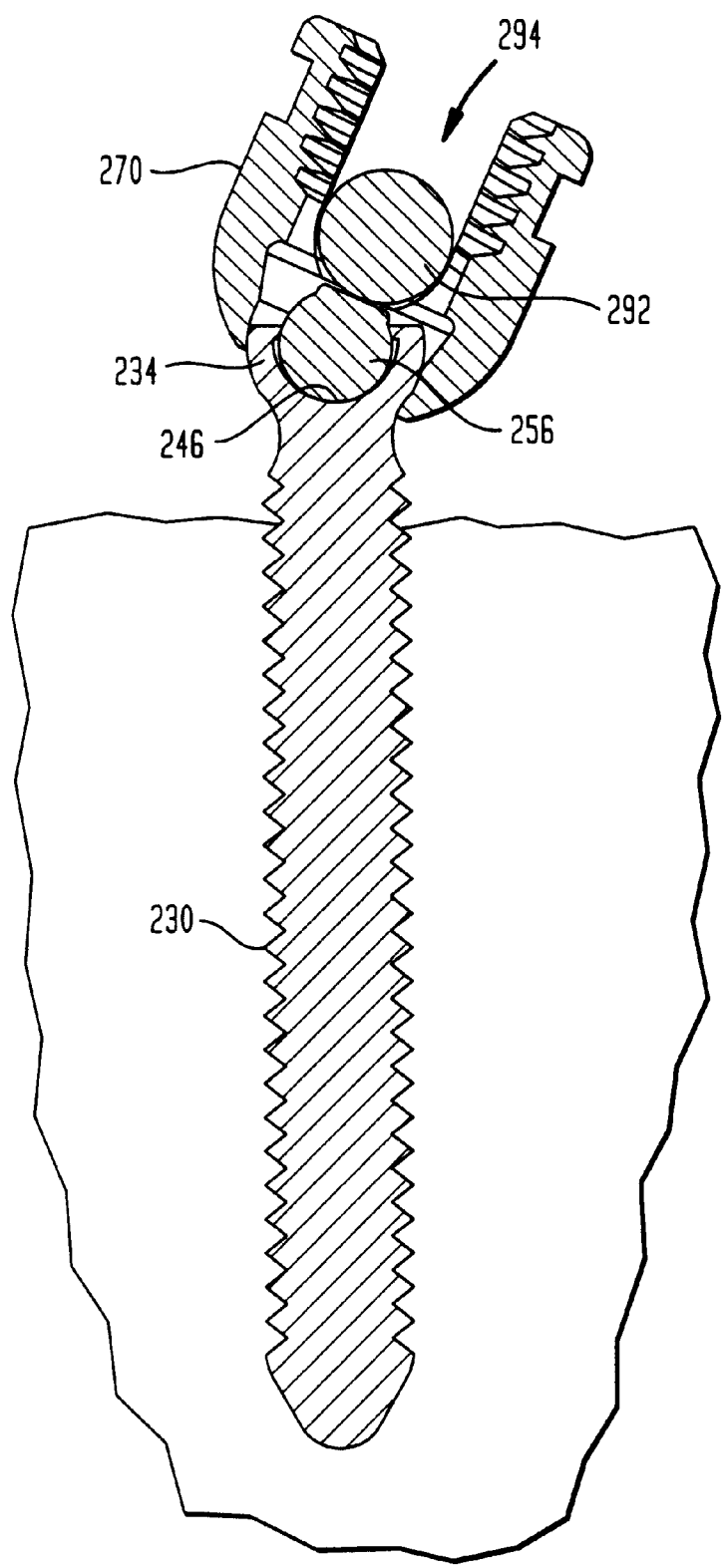
FIG. 22 shows a cross-sectional view of the pedicle screw assembly of FIG. 20C having an orthopedic rod secured in a rod receiving opening thereof, in accordance with preferred embodiments of the present invention.

Referring to FIGS. 20C and 21, the insert 256 is then positioned at least partially in the recess 246 of the expandable head 234. The insert 256 is retained in the recess 246 by the flexible arms 252 of the head 234. At this point, the insert 256 is free to rotate in the recess 246 and the coupling element 270 is free to pivot and rotate relative to the fastener 230. Referring to FIG. 22, after a rod 292 has been secured in the rod receiving opening 294, expansion of the expandable head 234 is effected when the rod 292 pushes the insert 256 further into the recess 246.

Figure 23:
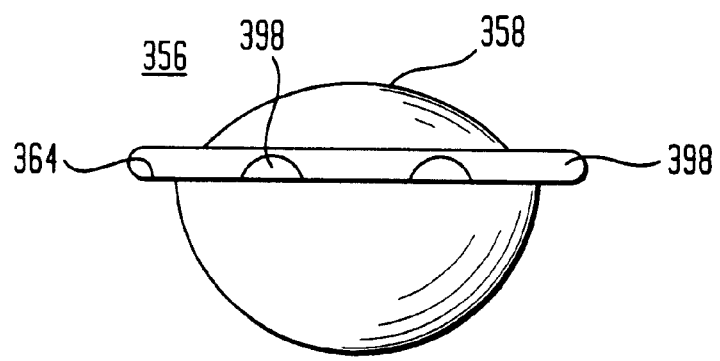
FIG. 23 shows a side view of an insert for a pedicle screw assembly in accordance with further preferred embodiments of the present invention.

FIG. 23 shows an insert 356 for a pedicle screw assembly in accordance with still other preferred embodiments of the present invention. The insert 356 has radial projections 398 at the upper end 358 thereof. The upper end 358 defines a surface having a radial curve for, inter alia, maintaining an orthopedic rod away from the head of the fastener (FIG. 1). The radial curve surface also facilitates movement of the fastener relative to the coupling element before the rod is secured in the coupling element. The insert includes a radial flange 364 for being secured by flexible arms of an expandable head as shown in FIGS. 10A–10C.

Figure 24:
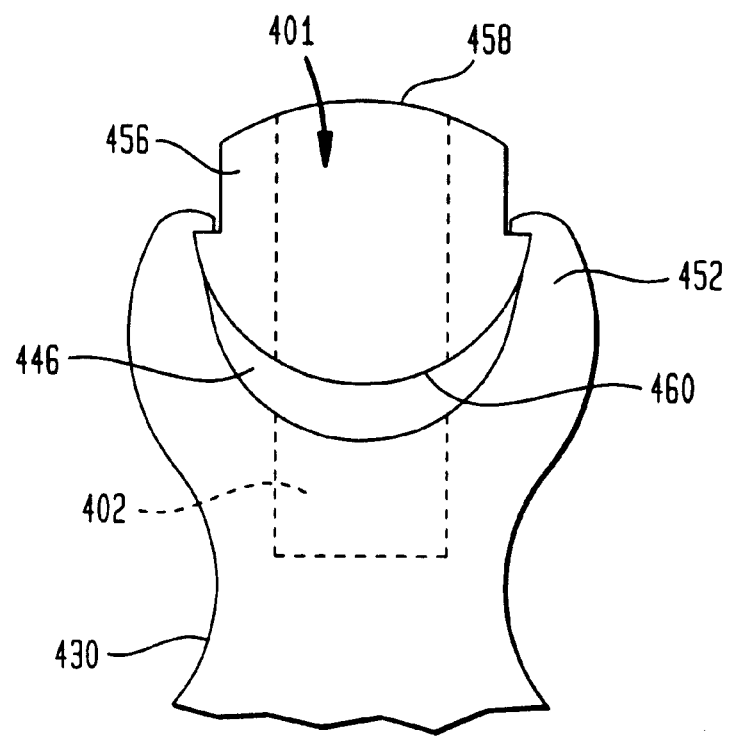
FIG. 24 shows a side view of an insert and a fastener for a pedicle screw assembly, in accordance with still further preferred embodiments of the present invention.

FIG. 24 shows a pedicle screw assembly in accordance with yet another preferred embodiment of the present invention. The assembly includes a fastener 430 substantially similar to the embodiment shown in FIGS. 1–3. The fastener 430 has an expandable head 434, a recess 446 formed in the expandable head and a plurality of flexible arms 452. The fastener 430 has a socket 402 formed at the bottom of the recess 446. A tool may be inserted in the socket for driving the fastener into bone. The assembly also preferably includes an insert 456 having a bore 404 extending from an upper end 458 to a lower end 460 thereof. The bore is preferably an axial bore 404 adapted for allowing the above-mentioned tool to pass therethrough and into the socket 402 at the bottom of the recess 446 for driving the fastener into bone.

Figure 25:
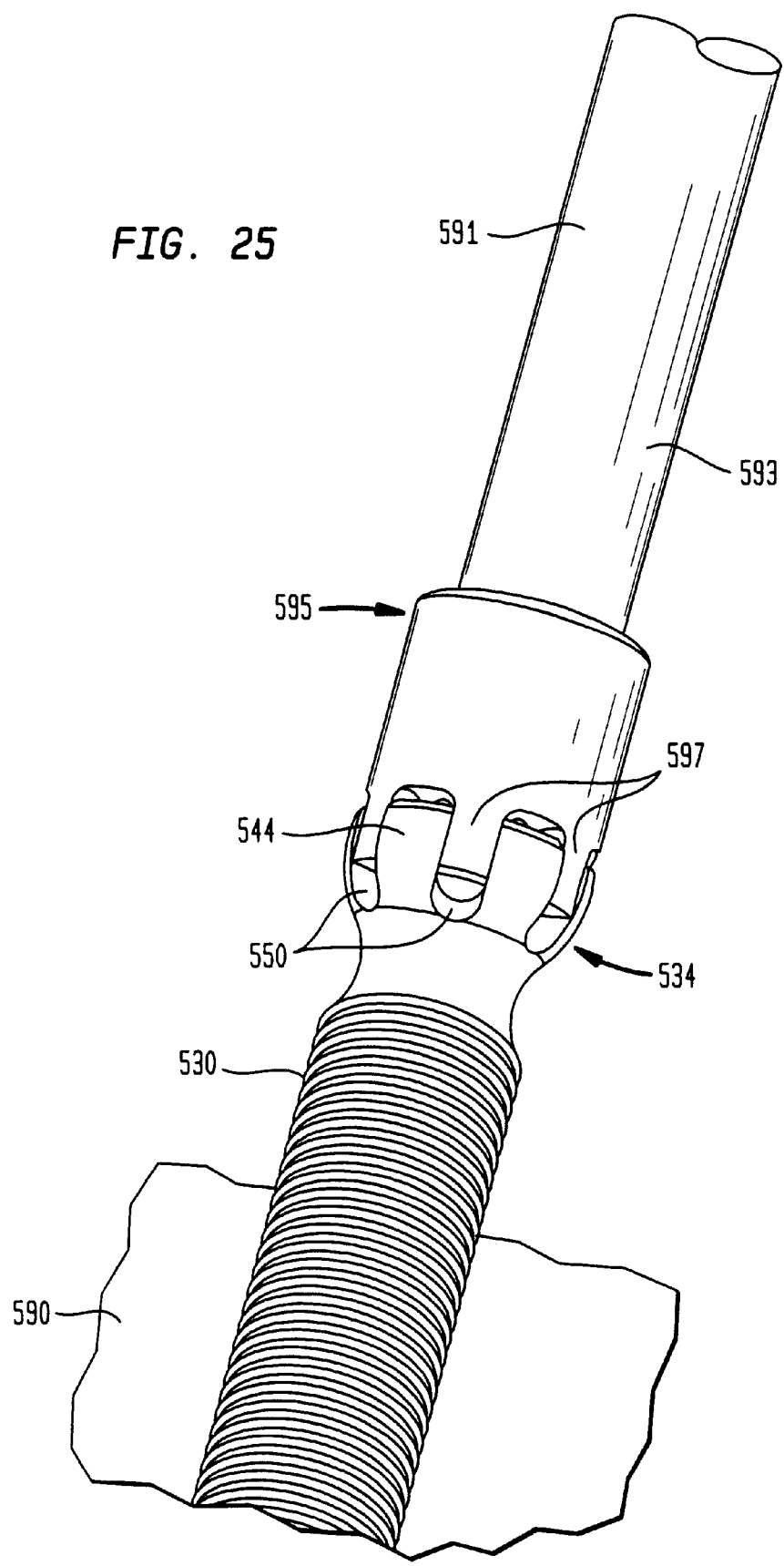
FIG. 25 shows a side view of a driver for driving a fastener of a pedicle screw assembly into bone, in accordance with certain preferred embodiments of the present invention.

Referring to FIG. 25, in one preferred embodiment, a driver 591 for driving a fastener 530 into bone includes a shaft 593 having a lower end 595 with a plurality of downwardly extending prongs 597. The prongs 597 are sized for fitting into the slots 550 of the head 534 of the fastener 530. Upon rotation of the shaft 593, the prongs 597 engage the flexible arms 544 of the head 534 for rotating the fastener and driving the fastener 530 into bone 590.

Figure 26:
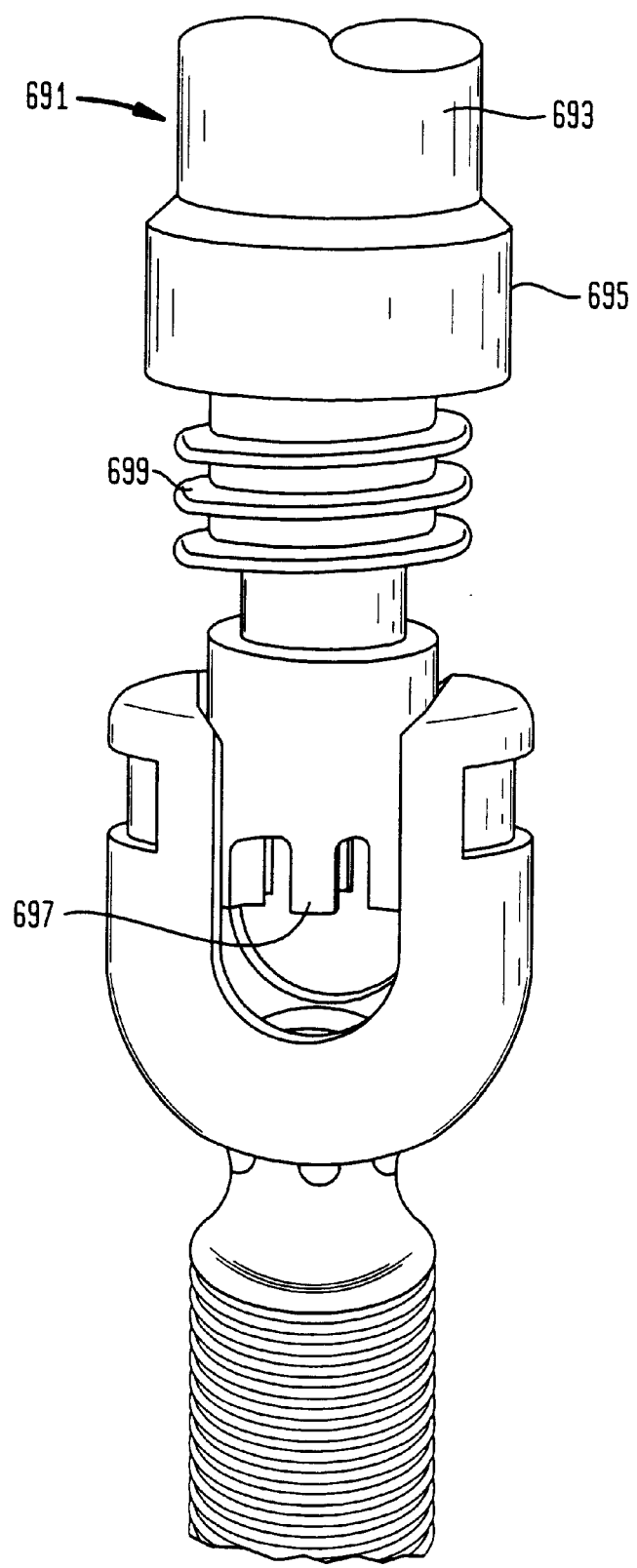
FIG. 26 shows a side view of a driver for driving a fastener of a pedicle screw assembly into bone, in accordance with further preferred embodiments of the present invention.
Figure 27:
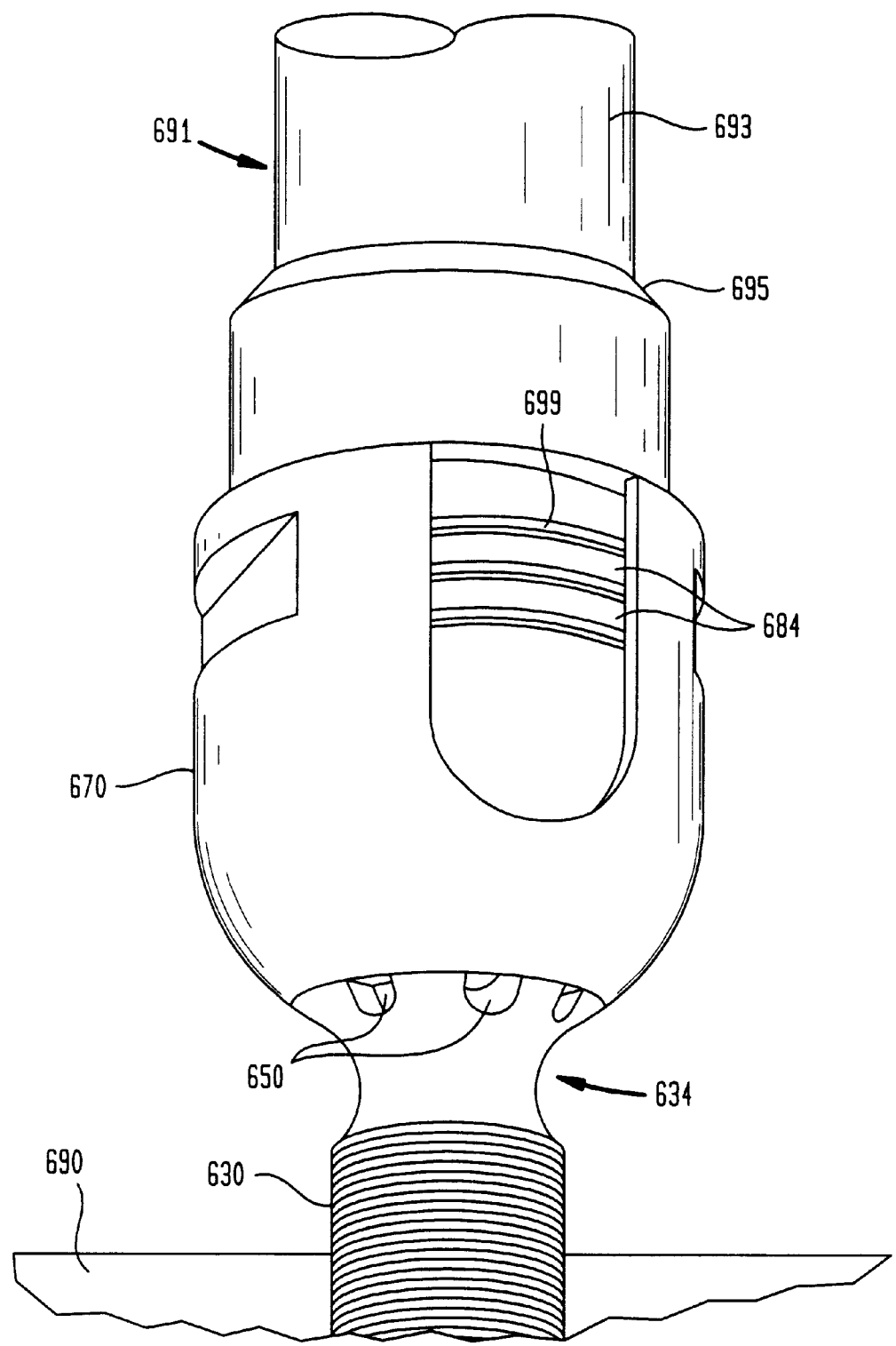
FIG. 27 shows the driver of FIG. 26 in engagement with the fastener.

FIGS. 26 and 27 show a driver 691 for driving a fastener 630 into bone 690 in accordance with further preferred embodiments of the present invention. The driver 691 is substantially similar to that shown in FIG. 25 and includes a shaft 693 with a lower end 695 and a plurality of downwardly extending prongs 697 sized to fit into the slots 650 of head 634. The driver includes external threads 699, preferably between the shaft 693 and the prongs 697 (FIG. 26). The external threads 699 are designed for threadably mating with internal threads 684 of coupling element 670. The mating engagement of the external threads 699 of the driver and the internal threads 684 generally stabilizes the entire pedicle screw assembly when driving the fastener 630 into bone 690.

As these and other variations and combinations of the features discussed above can be employed, the foregoing descriptions of the preferred embodiment should be taken by way of illustration rather than as limiting the invention as defined by the claims.

What is claimed is:

1. A pedicle screw assembly comprising:
   a. a fastener including a tip end for insertion into bone and an expandable head at the opposite end thereof, said head having an outer surface including a convex portion, and a recess having an inner surface and defining an inner dimension;
   b. an insert which can be positioned at least partially in the recess, said insert having an outer surface and defining an outer dimension that is greater than the inner dimension of the recess;
   c. a coupling element including a rod receiving opening, a bore for receiving said head of said fastener, and a seat for receiving said head of said fastener, said seat including a concave portion for receiving the convex portion of said head and allowing said fastener to pivot relative to said coupling element before being locked therein; and
   d. a locking element associated with said coupling element, said locking element being adapted to be forced against an orthopedic rod arranged in said rod receiving opening, to in turn force said insert into the recess of said head so that the outer dimension of said insert bears against the inner dimension of said head, whereby said head expands against the seat of said coupling element for preventing said coupling element from moving pivotally relative to said fastener.

2. The assembly as claimed in claim 1, wherein said head includes at least one slot extending between the inner and outer surfaces thereof for allowing expansion of said head.

3. The assembly as claimed in claim 2, wherein said fastener has a longitudinal axis.

4. The assembly as claimed in claim 2, wherein said at least one slot extends toward the tip end of said fastener.

5. The assembly as claimed in claim 3, wherein said at least one slot includes a plurality of slots.

6. The assembly as claimed in claim 5, wherein said plurality of slots subdivide said screw head into a plurality of flexible arms extending away from the tip end of said fastener.

7. The assembly as claimed in claim 6, wherein each said flexible arm includes a tab at an upper end thereof extending toward the longitudinal axis of said fastener.

8. The assembly as claimed in claim 7, wherein said at least one tab includes a plurality of tabs.

9. The assembly as claimed in claim 8, wherein said recess has an outer circumference and the plurality of tabs are arranged in an annular configuration around the outer circumference of said recess.

10. The assembly as claimed in claim 3, wherein the flexible arms of said head are adapted for flexing away from the longitudinal axis for expanding said head.

11. The assembly as claimed in claim 3, wherein the flexible arms of said head are adapted for flexing toward the longitudinal axis for compressing said head.

12. The assembly as claimed in claim 3, wherein the recess in said head is substantially centered on the longitudinal axis of said fastener.

13. The assembly as claimed in claim 3, wherein the inner and outer surfaces of said screw head are substantially centered on the longitudinal axis of said fastener.

14. The assembly as claimed in claim 8, wherein said insert has an upper end, a lower end and the outer surface extending therebetween, the outer surface of said insert including a flange.

15. The assembly as claimed in claim 14, wherein the tabs are adapted for engaging the flange for retaining said insert within the recess of said fastener.

16. The assembly as claimed in claim 8, wherein said insert has an upper end and an outer surface extending from the upper end that is substantially spherical in shape.

17. The assembly as claimed in claim 16, wherein said insert has a minimum diameter section adjacent the upper end and wherein the tabs are adapted for engaging the minimum diameter section for retaining said insert within the recess of said fastener.

18. The assembly as claimed in claim 1, wherein said insert has an upper end, a lower end and the outer surface extending therebetween, the outer surface of said insert including a flange for retaining said insert within said recess of said fastener.

19. The assembly as claimed in claim 18, wherein the outer surface of said insert tapers inwardly from the flange toward the lower end thereof.

20. The assembly as claimed in claim 19, wherein the lower end of said insert has a substantially spherical shape.

21. The assembly as claimed in claim 19, wherein the lower end of said insert is substantially flat.

22. The assembly as claimed in claim 18, wherein the upper end of said insert extends beyond said head for preventing said orthopedic rod from contacting said head.

23. The assembly as claimed in claim 18, wherein the upper end of said insert has a radial surface.

24. The assembly as claimed in claim 23, wherein the radial surface at the upper end of said insert is adapted for engaging said orthopedic rod.

25. The assembly as claimed in claim 18, wherein the outer surface of said insert is substantially conical.

26. The assembly as claimed in claim 18, wherein the outer surface of said insert is substantially polygon-shaped.

27. The assembly as claimed in claim 18, wherein the outer surface of said insert is substantially cylindrical.

28. The assembly as claimed in claim 1, wherein said insert includes at least one radial projection, whereby said at least one projection extends into said at least one slot when said insert is at least partially positioned in the recess.

29. The assembly as claimed in claim 28, wherein said at least one radial projection includes a plurality of radial projections.

30. The assembly as claimed in claim 18, wherein said insert includes a socket at an upper end thereof adapted for receiving a driver.

31. The assembly as claimed in claim 30, wherein the socket is adapted for receiving a hexagonal wrench.

32. The assembly as claimed in claim 30, wherein the socket is adapted for receiving a screwdriver.

33. The assembly as claimed in claim 1, wherein said insert includes an axial bore extending therethrough.

34. The assembly as claimed in claim 33, wherein the recess in said head includes a socket formed therein adapted to receive a driver for driving said fastener.

35. The assembly as claimed in claim 34, wherein when said insert is positioned in said recess, the axial bore of said insert is substantially aligned with the socket in the recess of said head.

36. The assembly as claimed in claim 1, wherein said insert has an upper end and an outer surface extending from the upper end that is substantially spherical in shape.

37. The assembly as claimed in claim 1, wherein said locking element comprises threads formed at an upper end of said coupling element.

38. The assembly as claimed in claim 37, wherein the coupling element threads are internal threads formed on an interior surface of said coupling element.

39. The assembly as claimed in claim 38, wherein said locking element further comprises a set screw having external threads for threadably engaging the internal threads of said coupling element.

40. The assembly as claimed in claim 37, wherein the coupling element threads are exterior threads formed on an exterior surface of said coupling element.

41. The assembly as claimed in claim 40, wherein said locking element further comprises a nut having internal threads for threadably engaging the exterior threads of said coupling element.

42. The assembly as claimed in claim 1, wherein the exterior surface of said coupling element includes one or more notches formed therein for securing said coupling element.

43. The assembly as claimed in claim 1, wherein said fastener includes a threaded portion having a diameter, the threaded portion extending from the tip end toward said head.

44. The assembly as claimed in claim 43, wherein said fastener includes a neck portion extending between the threaded portion thereof and said head, the neck portion having a diameter less than the diameter of the threaded portion for facilitating pivotal movement of said coupling element relative to said fastener.

45. The assembly as claimed in claim 44, wherein the neck of said fastener has a concave surface.

46. The pedicle screw assembly as claimed in claim 1, wherein said coupling element includes an exterior surface having a gripping surface.

47. The pedicle screw assembly as claimed in claim 1, wherein said coupling element includes an exterior surface having gripping means for maneuvering said coupling element.

48. The pedicle screw assembly as claimed in claim 47, wherein said gripping means includes one or more depressions formed in the exterior surface of said coupling element.

49. A driver for screwing the fastener of claim 5 into a bone, said driver comprising a shaft having a lower end and a plurality of prongs extending from the lower end of the shaft, wherein said prongs are adapted for being inserted into said slots.

50. The driver as claimed in claim 49, wherein said driver includes external threads provided on the shaft.

51. The driver as claimed in claim 50, wherein said locking element comprises internal threads formed on an interior surface of said coupling element.

52. The driver as claimed in claim 51, wherein the external threads of said driver are adapted for engaging the internal threads of said coupling element.

53. A pedicle screw assembly comprising:
  a. a fastener including a tip end for insertion into bone and a head at the opposite end thereof, said head having an outer surface with a convex portion and said head having a recess defining an inner surface having an inner dimension;
  b. an insert secured at least partially in said recess and having an outer surface in contact with the inner surface of said recess, wherein said insert pivots simultaneously with said fastener after being secured at least partially therein;
  c. a coupling element including a rod receiving opening, a bore for receiving said fastener, and a seat for receiving said head of said fastener, said seat including a concave portion for receiving the convex portion of said head and allowing said fastener to pivot relative to said coupling element before being locked therein; and
  d. a locking element for locking an orthopedic rod in the rod receiving opening, said locking element being associated with said coupling element to force said insert into the recess of said head so that the outer surface of said insert bears against the inner surface of said head, wherein said head engages the seat of said coupling element for preventing said coupling element from moving pivotally relative to said fastener.

54. The assembly as claimed in claim 53, wherein said head includes at least one slot extending between the inner and outer surfaces thereof for allowing expansion of said head.

55. The assembly as claimed in claim 54, wherein said at least one slot extends from an upper end of said fastener toward the tip end thereof.

56. The assembly as claimed in claim 55, wherein said at least one slot includes a plurality of slots.

57. The assembly as claimed in claim 54, wherein the outer surface of said insert includes an outer dimension that is greater than the inner dimension of the recess so that when said insert is forced into the recess the outer dimension of said insert bears against the inner dimension of said head for expanding said head.

58. The assembly as claimed in claim 57, wherein said insert has an upper end, a lower end and a flange therebetween extending around the outer dimension.

59. The pedicle screw assembly as claimed in claim 53, wherein said coupling element includes an exterior surface having a gripping surface.

60. The pedicle screw assembly as claimed in claim 53, wherein said coupling element includes an exterior surface having gripping means for maneuvering said coupling element.

61. The pedicle screw assembly as claimed in claim 60, wherein said gripping means includes one or more depressions formed in the exterior surface of said coupling element.

62. A pedicle screw assembly for use in conjunction with an orthopedic rod, said assembly comprising:
   a. a fastener including a tip end for insertion into bone and an expandable head at the opposite end thereof having an outer surface including a convex portion, a recess formed in said head defining an inner surface having an inner dimension; and
   b. a coupling element including a rod receiving opening, a bore for receiving said fastener, and a seat for receiving said head of said fastener, said seat including a concave portion for receiving the convex portion of said head and allowing said fastener to pivot relative to said coupling element before being locked therein.

63. The assembly as claimed in claim 62, wherein said expandable head includes at least one slot extending between the inner and outer surfaces of said head for allowing expansion of said head.

64. The assembly as claimed in claim 63, wherein said at least one slot extends from an upper end of said fastener toward the tip end thereof.

65. The assembly as claimed in claim 64, wherein said at least one slot includes a plurality of slots.

66. The assembly as claimed in claim 65, wherein said plurality of slots subdivide said head into a plurality of flexible arms at the upper end of said fastener.

67. The assembly as claimed in claim 66, wherein said flexible arms are adapted for flexing away from one another for expanding said screw head.

68. The assembly as claimed in claim 67, further comprising an insert which can be positioned at least partially in the recess, said insert having an outer dimension that is greater than the inner dimension of said head.

69. The assembly as claimed in claim 62, wherein said coupling element includes an exterior surface having one or more notches formed therein for securing said coupling element.

70. The assembly as claimed in claim 68, further comprising a locking element for locking an orthopedic rod in the rod receiving opening, said locking element being associated with said coupling element to force said insert into the recess of said head so that the outer dimension of said insert bears against the inner dimension of said head, wherein said head expands against the seat of said coupling element for preventing said fastener from moving pivotally relative to said coupling element.

71. The pedicle screw assembly as claimed in claim 62, wherein said coupling element includes an exterior surface having a gripping surface.

72. The pedicle screw assembly as claimed in claim 62, wherein said coupling element includes an exterior surface having gripping means for maneuvering said coupling element.

73. The pedicle screw assembly as claimed in claim 72, wherein said gripping means includes one or more depressions formed in the exterior surface of said coupling element.

74. A pedicle screw assembly comprising:
   a. a fastener including a tip end for insertion into bone and an expandable head at the opposite end thereof, said head including an outer surface having an outer dimension and a recess having an inner surface, the inner surface defining an inner dimension of said head; and
   b. a coupling element including a rod receiving opening, a bore having upper and lower ends for receiving said fastener, and a seat for receiving said head of said fastener, the bore having a minimum diameter section with an inner dimension that is less than the outer dimension of said head and defining an expansion cavity between the upper and lower ends thereof having an inner dimension greater than the outer dimension of said head, wherein said screw can be pivotally connected with said coupling element by passing the tip end of said fastener through the upper end of said bore toward the lower end thereof while compressing said head as said head passes through the minimum diameter section of said bore.

75. The assembly as claimed in claim 74, wherein said expandable head includes at least one slot extending between the inner and outer surfaces thereof for allowing expansion and compression of said expandable head.

76. The pedicle screw assembly as claimed in claim 74, wherein said coupling element includes an exterior surface having a gripping surface.

77. The pedicle screw assembly as claimed in claim 74, wherein said coupling element includes an exterior surface having gripping means for maneuvering said coupling element.

78. The pedicle screw assembly as claimed in claim 77, wherein said gripping means includes one or more depressions formed in the exterior surface of said coupling element.

* * * * *